US012661189B2

(12) United States Patent
Luengo Muntion et al.

(10) Patent No.: US 12,661,189 B2
(45) Date of Patent: Jun. 23, 2026

(54) PREDICTION OF STRUCTURES IN SURGICAL DATA USING MACHINE LEARNING

(71) Applicant: DIGITAL SURGERY LIMITED, London (GB)

(72) Inventors: Imanol Luengo Muntion, London (GB); Danail V. Stoyanov, London (GB); Andre Chow, London (GB); Petros Giataganas, Croydon (GB); David P. Owen, London (GB); Maria Grammatikopoulou, London (GB); Ricardo Sanchez-Matilla, London (GB); Maria Ruxandra Robu, London (GB)

(73) Assignee: DIGITAL SURGERY LIMITED, London (GB)

( * ) Notice: Subject to any disclaimer, the term of this patent is extended or adjusted under 35 U.S.C. 154(b) by 85 days.

(21) Appl. No.: 18/282,655

(22) PCT Filed: Mar. 18, 2022

(86) PCT No.: PCT/GR2022/000013
§ 371 (c)(1),
(2) Date: Sep. 18, 2023

(87) PCT Pub. No.: WO2022/195303
PCT Pub. Date: Sep. 22, 2022

(65) Prior Publication Data
US 2024/0169579 A1     May 23, 2024

Related U.S. Application Data

(60) Provisional application No. 63/213,815, filed on Jun. 23, 2021, provisional application No. 63/212,157, (Continued)

(51) Int. Cl.
A61B 34/00          (2016.01)
A61B 34/20          (2016.01)
(Continued)

(52) U.S. Cl.
CPC .............. A61B 34/25 (2016.02); A61B 34/20 (2016.02); A61B 90/37 (2016.02); G06T 7/0012 (2013.01);
(Continued)

(58) Field of Classification Search
CPC ......... A61B 34/25; A61B 34/20; A61B 90/37; A61B 2034/107; A61B 2034/2065;
(Continued)

(56) References Cited

U.S. PATENT DOCUMENTS 9,123,155 B2     9/2015   Cunningham et al.
9,788,907 B1     10/2017  Alvi et al.
(Continued)

FOREIGN PATENT DOCUMENTS

CA          3107582 A1      1/2020
CN          101696943 A     4/2010
(Continued)

OTHER PUBLICATIONS

Colleoni et al., "Deep Learning Based Robotic Tool Detection and Articulation Estimation with Spatio-Temporal Layers", IEEE Robotics and Automation Letters, Jul. 1, 2019, 7 pages.
(Continued)

*Primary Examiner* — William A Beutel
(74) *Attorney, Agent, or Firm* — CANTOR COLBURN LLP; Robert Crist

(57) ABSTRACT

A location of an anatomical structure in image(s) from a surgical procedure is predicted using machine learning. An image/video capture device such as an endoscope, a wearable camera, a stationary camera, etc., can be used to capture
(Continued)

*200*

| Predict phases in the surgical procedure | 202 |
| Predict location of anatomical structural data in surgical data | 204 |
| Predict location of surgical instruments in the surgical data | 206 |
| Generate augmented visualization of the surgical view | 208 |
| Determine whether surgical instrument is within predetermined proximity of a critical anatomical structure | 210 |
| Take preventive actions including displaying alarm, alert, adjusting surgical instruments, etc., if required in the augmented visualization | 212 | the image(s). A confidence score of the prediction of the machine learning is determined. A surgeon can be provided an augmented visualization of the surgical procedure by displaying one or more graphical overlays based on the findings of the machine learning to enhance the surgeon-s information.

20 Claims, 15 Drawing Sheets

Related U.S. Application Data filed on Jun. 18, 2021, provisional application No. 63/211,139, filed on Jun. 16, 2021, provisional application No. 63/211,100, filed on Jun. 16, 2021, provisional application No. 63/211,098, filed on Jun. 16, 2021, provisional application No. 63/163,417, filed on Mar. 19, 2021, provisional application No. 63/163,425, filed on Mar. 19, 2021.

(51) Int. Cl.

| | |
|---|---|
| *A61B 90/00* | (2016.01) |
| *G06T 7/00* | (2017.01) |
| *G06T 7/20* | (2017.01) |
| *G06T 7/50* | (2017.01) |
| *G06T 7/70* | (2017.01) |
| *G06T 11/00* | (2006.01) |
| *G06T 11/10* | (2026.01) |
| *G06V 10/26* | (2022.01) |
| *G06V 10/774* | (2022.01) |
| *G06V 20/40* | (2022.01) |
| *G06V 20/50* | (2022.01) |
| *G16H 30/40* | (2018.01) |
| *A61B 34/10* | (2016.01) |

(52) U.S. Cl.
CPC .................. *G06T 7/20* (2013.01); *G06T 7/50* (2017.01); *G06T 7/70* (2017.01); *G06T 11/00* (2013.01); *G06T 11/10* (2026.01); *G06V 10/26* (2022.01); *G06V 10/774* (2022.01); *G06V 20/41* (2022.01); *G06V 20/50* (2022.01); *G16H 30/40* (2018.01); *A61B 2034/107* (2016.02); *A61B 2034/2065* (2016.02); *A61B 2034/252* (2016.02); *A61B 2090/364* (2016.02); *G06T 2207/10016* (2013.01); *G06T 2207/20081* (2013.01); *G06T 2207/30004* (2013.01); *G06T 2210/41* (2013.01); *G06V 2201/031* (2022.01); *G06V 2201/034* (2022.01)

(58) Field of Classification Search
CPC ........ A61B 2034/252; A61B 2090/364; A61B 2017/00026; A61B 2017/00119; A61B 90/36; A61B 2090/365; A61B 2090/371; A61B 2090/372; G06T 7/0012; G06T 7/20; G06T 7/50; G06T 7/70; G06T 11/00; G06T 11/001; G06T 2207/10016; G06T 2207/20081; G06T 2207/30004; G06T 2210/41; G06T 7/11; G06T 2207/10068; G06T 7/74; G06T 2207/20084; G06V 10/26; G06V 10/774; G06V 20/41; G06V 20/50; G06V 2201/031; G06V 2201/034; G06V 2201/03; G16H 30/40; G16H 20/40; G16H 40/20; G16H 40/67; G16H 50/20; G16H 50/70; G16H 70/20; G06F 18/24133
See application file for complete search history.

(56) References Cited

U.S. PATENT DOCUMENTS

| | | | |
|---|---|---|---|
| 10,152,789 | B2 | 12/2018 | Carnes et al. |
| 10,251,714 | B2 | 4/2019 | Carnes et al. |
| 10,356,385 | B2 | 7/2019 | Petrichkovich et al. |
| 10,383,694 | B1 | 8/2019 | Venkataraman |
| 10,579,878 | B1 | 3/2020 | Bauer |
| 10,956,790 | B1 | 3/2021 | Victoroff et al. |
| 11,189,379 | B2 | 11/2021 | Giataganas et al. |
| 11,246,664 | B2 | 2/2022 | Andrews et al. |
| 11,263,772 | B2 | 3/2022 | Siemionow et al. |
| 11,311,342 | B2 | 4/2022 | Parihar et al. |
| 11,322,248 | B2 | 5/2022 | Grantcharov et al. |
| 11,370,113 | B2 | 6/2022 | Habbecke et al. |
| 11,464,583 | B2 | 10/2022 | Sano et al. |
| 11,497,557 | B2 | 11/2022 | Haslam et al. |
| 11,564,756 | B2 | 1/2023 | Shelton, IV et al. |
| 11,602,398 | B2 | 3/2023 | Regensburger |
| 11,622,818 | B2 | 4/2023 | Siemionow et al. |
| 11,910,995 | B2 | 2/2024 | Hendriks et al. |
| 11,915,378 | B2 | 2/2024 | Koza et al. |
| 11,977,998 | B2 | 5/2024 | Stiller et al. |
| 12,062,442 | B2 | 8/2024 | Shelton, IV |
| 12,136,220 | B2 | 11/2024 | Vasilev et al. |
| 12,150,719 | B2 | 11/2024 | Wright et al. |
| 12,161,430 | B2 | 12/2024 | Wright et al. |
| 12,198,330 | B2 | 1/2025 | Blau |
| 12,217,427 | B2 | 2/2025 | Schreckenberg et al. |
| 12,220,174 | B2 | 2/2025 | Khan et al. |
| 12,226,163 | B2 | 2/2025 | Besier et al. |
| 12,290,938 | B2 | 5/2025 | Wright et al. |
| 12,327,351 | B2 | 6/2025 | Pai Raikar et al. |
| 12,360,351 | B2 | 7/2025 | Segev et al. |
| 12,380,998 | B2 | 8/2025 | Giataganas et al. |
| 2007/0136218 | A1 | 6/2007 | Bauer |
| 2009/0036902 | A1 | 2/2009 | Dimaio |
| 2010/0167248 | A1 | 7/2010 | Ryan |
| 2012/0020547 | A1 | 1/2012 | Zhao et al. |
| 2013/0288214 | A1 | 10/2013 | Kesavadas |
| 2013/0295540 | A1 | 11/2013 | Kesavadas |
| 2014/0107471 | A1 | 4/2014 | Haider et al. |
| 2014/0286533 | A1 | 9/2014 | Luo |
| 2014/0350391 | A1 | 11/2014 | Prisco et al. |
| 2015/0297313 | A1 | 10/2015 | Reiter |
| 2017/0020395 | A1 | 1/2017 | Malchano et al. |
| 2017/0105713 | A1 | 4/2017 | Frimer |
| 2018/0032130 | A1 | 2/2018 | Meglan |
| 2018/0065248 | A1* | 3/2018 | Barral ..................... B25J 9/163 |
| 2018/0071032 | A1 | 3/2018 | De Almeida Barreto |
| 2018/0243906 | A1 | 8/2018 | Hourtash |
| 2018/0247128 | A1 | 8/2018 | Alvi et al. |
| 2018/0271603 | A1 | 9/2018 | Nir |
| 2018/0296075 | A1 | 10/2018 | Meglan et al. |
| 2018/0310811 | A1 | 11/2018 | Meglan et al. |
| 2018/0310875 | A1 | 11/2018 | Meglan et al. |
| 2018/0322949 | A1 | 11/2018 | Mohr et al. |
| 2018/0325604 | A1 | 11/2018 | Atarot |
| 2019/0008587 | A1 | 1/2019 | Allison et al. |
| 2019/0029766 | A1 | 1/2019 | Griffiths et al. |
| 2019/0038362 | A1 | 2/2019 | Nash et al. |
| 2019/0046276 | A1 | 2/2019 | Inglese et al. |
| 2019/0053872 | A1 | 2/2019 | Meglan |
| 2019/0088162 | A1 | 3/2019 | Meglan |
| 2019/0090954 | A1 | 3/2019 | Kotian et al. |
| 2019/0099226 | A1 | 4/2019 | Hallen |
| 2019/0251723 | A1 | 8/2019 | Coppersmith, III et al. |
| 2019/0325574 | A1* | 10/2019 | Jin ....................... G06V 10/751 |
| 2020/0036797 | A1 | 1/2020 | Kudelski |
| 2020/0226751 | A1 | 7/2020 | Jin et al. |
| 2021/0015554 | A1 | 1/2021 | Chow |
| 2021/0183124 | A1 | 6/2021 | Benditte-Klepetko |
| 2022/0000565 | A1 | 1/2022 | Gururaj et al. |
| 2022/0044440 | A1 | 2/2022 | Blau |
| 2023/0024942 | A1 | 1/2023 | Wright et al. |
| 2023/0029184 | A1 | 1/2023 | Wright et al. |
| 2023/0047100 | A1 | 2/2023 | Arcadu et al. |
| 2023/0074481 | A1 | 3/2023 | Pai Raikar et al. |

(56)        References Cited

U.S. PATENT DOCUMENTS

| | | |
|---|---|---|
| 2023/0098859 A1 | 3/2023 | Kitamura et al. |
| 2023/0105111 A1 | 4/2023 | Nickel et al. |
| 2023/0268051 A1 | 8/2023 | Wachs et al. |
| 2024/0156547 A1 | 5/2024 | Luengo Muntion et al. |
| 2024/0161497 A1 | 5/2024 | Luengo Muntion et al. |
| 2024/0206989 A1 | 6/2024 | Luengo Muntion et al. |
| 2024/0303984 A1 | 9/2024 | Sanchez-Matilla et al. |

FOREIGN PATENT DOCUMENTS

| | | |
|---|---|---|
| CN | 103142313 B | 5/2015 |
| CN | 108024833 A | 5/2018 |
| CN | 111261252 A | 6/2020 |
| JP | 2018029961 A | 3/2018 |
| WO | 2017098504 A | 6/2017 |
| WO | 2018005842 A1 | 1/2018 |
| WO | 2018217433 A1 | 11/2018 |
| WO | 2018217444 A2 | 11/2018 |
| WO | 2018237187 A2 | 12/2018 |
| WO | 2019036006 A1 | 2/2019 |
| WO | 2019036007 A1 | 2/2019 |
| WO | 2019050729 A1 | 3/2019 |
| WO | 2019050886 A1 | 3/2019 |
| WO | 2019139949 A1 | 7/2019 |
| WO | 2019217893 A1 | 11/2019 |
| WO | 2020009830 A1 | 1/2020 |
| WO | 2020102584 A2 | 5/2020 |
| WO | 2021058294 A1 | 4/2021 |

OTHER PUBLICATIONS

Extended European Search Report for Application No. 19220289.3-1207 issued Nov. 24, 2020, 12 pages.

Hashimoto, et al., Artificial Intelligence in Surgery: Promises and Perils, Jul. 2018, 15 pages.

International Search Report and Written Opinion for PCT/GR2022/000013; International Filing Date Mar. 18, 2022; Date of Mailing: Jun. 22, 2022; 9 pages.

International Search Report and Written Opinion for PCT/GR2022/000014; International Filing Date Mar. 18, 2022; Date of Mailing: Jun. 20, 2022; 8 pages.

International Search Report and Written Opinion for PCT/GR2022/000015; International Filing Date Mar. 18, 2022; Date of Mailing: Jun. 14, 2022; 11 pages.

International Search Report and Written Opinion for PCT/GR2022/000016; International Filing Date Mar. 18, 2022; Date of Mailing: Jun. 22, 2022; 14 pages.

Islam et al., "AP-MTL: Attention Pruned Multi-task Learning Model for Real-time Instrument Detection and Segmentation in Robot-assisted Surgery", 2020 IEEE International Conference on Robotics and Automation, May 31, 2020, pp. 8433-8439.

Jin et al., "Multi-task recurrent convolutional network with correlation loss for surgical video analysis", Medical Image Analysis, Oct. 2019, 31 pages.

Sarikaya et al., "Detection and Localization of Robotic Tools in Robot-Assisted Surgery Videos Using Deep Neural Networks for Region Proposal and Detection", Cornell University Library, Jul. 2020, 8 pages.

Twinanda et al, "EndoNet: A Deep Architecture for Recognition Tasks on Laparoscopic Videos", IEEE Transactions, Jan. 2017; 11 pages.

Yang et el., Image-based laparoscopic tool detection and tracking using convolutional neural networks: a review of the literature, Computer Assisted Surgery, Jan. 2020, pp. 15-28.

Yidan et al., "daVinciNet: Joint Prediction of Motion and Surgical State in Robot-Assisted Surgery" 2020 IEEE International Conference; Oct. 2020; 8 pages.

Yidan et al., "Temporal Segmentation of Surgical Sub-tasks through Deep Learning with Multiple Data Sources", 2020 IEEE International Conference, May 2020, 12 pages.

Qin et al. "daVinciNet: Joint Prediction of Motion and Surgical Sate in Robot-Assisted Surgery" 2020, arxiv.org, Cornell University Library, XP081771349 (16 Pages).

European Examination Report, Dated: Aug. 5, 2025, Application No. 22714529.9-1218, Filed: Mar. 18, 2022, 9 pages.

* cited by examiner

Surgical
Instrument
504

503

Graphic Overlay
Critical Anatomical Structure
502

501

502
Graphic Overlay
Representing Alert

502
Graphic Overlay Over
A Surgical Instrument

Heatmap + Self-supervised 1106

Heatmap 1104

Segmentation 1102

Grasping gallbladder
1202

Dissecting fat
1204

Dissecting fat
1206

Clipping Structure
1208

Critical view of safety
1210

After division
1212

PREDICTION OF STRUCTURES IN SURGICAL DATA USING MACHINE LEARNING

CROSS REFERENCE TO RELATED APPLICATIONS

This application is a National Stage application of PCT/GR2022/000013, filed Mar. 18, 2022, which claims the benefit of U.S. Provisional 63/211,098, filed on Jun. 16, 2021, which is incorporated by reference in its entirety for all purposes. This application also claims the benefit of and priority to U.S. Provisional Application No. 63/211,139, filed on Jun. 16, 2021, which is incorporated by reference in its entirety for all purposes. This application also claims the benefit of and priority to U.S. Provisional Application No. 63/211,100, filed on Jun. 16, 2021, which is incorporated by reference in its entirety for all purposes. This application also claims the benefit of and priority to U.S. Provisional Application No. 63/212,157, filed on Jun. 18, 2021, which is incorporated by reference in its entirety for all purposes. This application also claims the benefit of and priority to U.S. Provisional Application No. 63/213,815, filed on Jun. 23, 2021, which is incorporated by reference in its entirety for all purposes. This application also claims the benefit of and priority to U.S. Provisional Patent Application No. 63/163,417, filed Mar. 19, 2021 and U.S. Provisional Patent Application No. 63/163,425, filed Mar. 19, 2021, which are incorporated by reference in their entirety for all purposes.

BACKGROUND

The present disclosure relates in general to computing technology and relates more particularly to computing technology for automatic detection and visualization of structures in surgical data using machine learning prediction, and providing user feedback based on the automatic detection.

Computer-assisted systems can be useful to augment a person's physical sensing, perception, and reaction capabilities. For example, such systems can effectively provide information corresponding to an expanded field of vision, both temporal and spatial, that enables a person to adjust current and future actions and decisions based on the part of an environment not included in his or her physical field of view. Additionally, the systems can bring attention to occluded parts of the view, for example due to structures, blood, etc. However, providing such information relies upon an ability to process part of this extended field in a useful manner. Highly variable, dynamic, and/or unpredictable environments present challenges in defining rules that indicate how representations of the environments are to be processed to output data to productively assist the person in action performance.

SUMMARY

According to one or more aspects, a computer-implemented method includes predicting, by a first machine learning model, a location of an anatomical structure in an input window comprising one or more images from a video of a surgical procedure, the first machine learning model is trained using surgical training data. The method further includes predicting, by a second machine learning model, a location of a surgical instrument in the input window, the second machine learning model is trained using the surgical training data. The method further includes generating a visualization of the surgical procedure by displaying a first graphical overlay at the location of the anatomical structure and a second graphical overlay at the location of the surgical instrument in the video of the surgical procedure. The method further includes, based on a determination that the location of the surgical instrument is within a predetermined threshold from the location of the anatomical structure, providing a user feedback to indicate a proximity of the surgical instrument and the anatomical structure.

In one or more examples, the first machine learning model is trained to predict the location of the anatomical structure associated with a particular type of the surgical procedure.

In one or more examples, the first machine learning model predicts the location of the anatomical structure based on an identification of a phase of the surgical procedure being performed.

In one or more examples, the second machine learning model is trained to predict the location of the surgical instrument associated with a particular type of the surgical procedure.

In one or more examples, the second machine learning model predicts the location of the surgical instrument based on an identification of a phase of the surgical procedure being performed.

In one or more examples, determining the proximity of the surgical instrument and the anatomical structure comprises predicting, by a third machine learning model, a depth map of a field of view of the video.

In one or more examples, the user feedback is provided based on the anatomical structure being determined as a critical anatomical structure based on a type of the surgical procedure.

In one or more examples, the user feedback is provided based on the anatomical structure being determined as a critical anatomical structure based on one or more attributes of a patient undergoing the surgical procedure.

In one or more examples, the first machine learning model uses weak labels. In one or more examples, the second machine learning model uses weak labels. In one or more examples, the second machine learning model uses joint detection and segmentation (with/without weak labels).

According to one or more examples, a system includes a machine learning training system configured to use a training dataset to train a first machine learning model to predict a location of an anatomical structure in images from the training dataset. The machine learning training system also trains a second machine learning model to predict a location of a surgical instrument in the images from the training dataset. The system further includes a data collection system to capture a video of a surgical procedure. The system also includes a model execution system to execute the first machine learning model and the second machine learning model to detect the location of the anatomical structure and the location of the surgical instrument in an input window of the video. The system further includes an output generator to generate a visualization of the surgical procedure by displaying a first graphical overlay at the location of the anatomical structure in the video of the surgical procedure. The output generator also, based on a determination that the location of the surgical instrument is within a predetermined threshold from the location of the anatomical structure, provides a user feedback by generating a second graphical overlay to indicate a proximity of the surgical instrument and the anatomical structure by displaying the second graphical overlay in the visualization of the surgical procedure.

In one or more examples, the first machine learning model is trained to predict the location of the anatomical structure associated with a particular type of the surgical procedure.

In one or more examples, the first machine learning model predicts the location of the anatomical structure based on an identification of a phase of the surgical procedure being performed.

In one or more examples, the machine learning training system is further configured to train a third machine learning model to predict a depth map of the images from the training dataset. Further, the model execution system is further configured to execute the third machine learning model to predict the depth map of a field of view of the video. Also, the depth map is used to determine that the location of the surgical instrument is within the predetermined threshold from the location of the anatomical structure.

In one or more examples, the output generator is further configured to determine a movement vector based on a change in the location of the anatomical structure in the input window of the video. Further, the location of the anatomical structure in a portion of the video that is captured after the input window is predicted based on the movement vector. Also, the first graphical overlay is displayed in the visualization of the video at the predicted location of the anatomical structure.

According to one or more aspects, a computer program product includes a memory device having computer executable instructions stored thereon, which when executed by one or more processors cause the one or more processors to perform a method for prediction of features in surgical data using machine learning. The method includes predicting, using an encoder-decoder model, a location of an anatomical structure in an input window comprising one or more images from a video of a surgical procedure, the encoder-decoder model is trained using surgical training data, wherein the encoder-decoder model predicts the location of the anatomical structure based on an identification of a phase of the surgical procedure being performed. The method further includes determining a confidence score of the prediction of the location of the anatomical structure. The method further includes generating a visualization of the surgical procedure by displaying a graphical overlay at the location of the anatomical structure in the video of the surgical procedure, one or more visual attributes of the graphical overlay are configured based on the confidence score.

In one or more examples, the identification of the phase of the surgical procedure being performed is determined by a machine learning model from the video of the surgical procedure.

In one or more examples, the encoder-decoder model is a first encoder-decoder model, and the method further includes predicting, by a second encoder-decoder model, a location of a surgical instrument in the input window, the second encoder-decoder model is trained using the surgical training data. Further, based on a determination that the location of the surgical instrument is within a predetermined threshold from the location of the anatomical structure, a user feedback is provided in the visualization.

In one or more examples, the user feedback is provided by generating, in the visualization of the surgical procedure, a second graphical overlay indicative of a proximity of the surgical instrument and the anatomical structure.

In one or more examples, determining the proximity of the surgical instrument and the anatomical structure comprises, predicting, by a machine learning model, a depth map of a field of view of the video.

In one or more examples, the user feedback is provided based on the anatomical structure being determined as a critical anatomical structure for the surgical procedure being performed.

According to one or more aspects, a system includes a memory device, and one or more processors coupled with the memory device. The one or more processors configured to perform a method that includes predicting, using machine learning, based on an input window comprising one or more images from a video of a surgical procedure, a phase being performed within the surgical procedure. The method further includes predicting, using machine learning, a location of an anatomical structure in the input window based on the phase of the surgical procedure. The method further includes determining a confidence score of the prediction of the location of the anatomical structure. The method further includes outputting the location of the anatomical structure and the confidence score.

In one or more examples, the method further comprises, generating a visualization of the surgical procedure by displaying a graphical overlay at the location of the anatomical structure in the video of the surgical procedure, one or more visual attributes of the graphical overlay are configured based on the confidence score.

In one or more examples, the one or more visual attributes of the graphical overlay comprise color, transparency, shading pattern, and outline.

According to one or more aspects, a computer-implemented method includes predicting, using machine learning, a location of an anatomical structure in an input window comprising one or more images from a video of a surgical procedure, the first machine learning model trained using surgical training data. The method further includes computing, using machine learning, a confidence score of the prediction of the location of the anatomical structure. The method further includes generating a visualization of the surgical procedure by displaying a graphical overlay at the location of the anatomical structure in the video of the surgical procedure, wherein one or more visual attributes of the graphical overlay are configured based on the confidence score.

In one or more examples, the one or more visual attributes of the graphical overlay comprise color, transparency, shading pattern, text, and outline.

In one or more examples, the graphical overlay is displayed in response to the anatomical structure being determined as a critical anatomical structure based for the surgical procedure.

Additional technical features and benefits are realized through the techniques of the present invention. Aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the aspects of the invention are apparent from the following detailed description taken in conjunction with the accompanying drawings in which:

Figure 1:
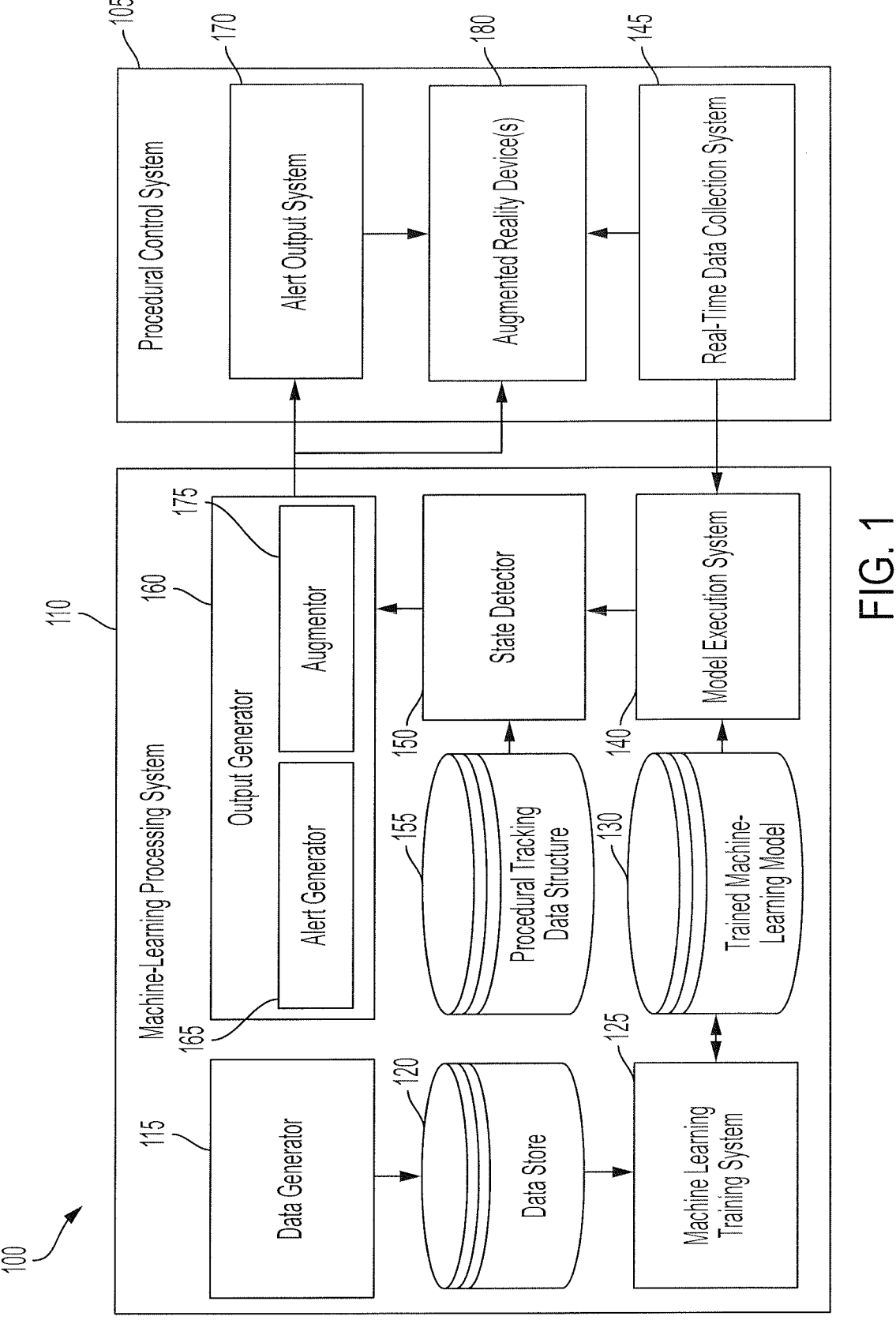
FIG. 1 shows a system for predicting structures in surgical data using machine learning according to one or more aspects.

The diagrams depicted herein are illustrative. There can be many variations to the diagram, or the operations described therein without departing from the spirit of the invention. For instance, the actions can be performed in a differing order, or actions can be added, deleted, or modified. Also, the term "coupled", and variations thereof describe having a communications path between two elements and do not imply a direct connection between the elements with no intervening elements/connections between them. All of these variations are considered a part of the specification.

DETAILED DESCRIPTION

Exemplary aspects of technical solutions described herein relate to, among other things, devices, systems, methods, computer-readable media, techniques, and methodologies for using machine learning and computer vision to automatically predict, or detect, one or more structures in surgical data, the structures being deemed to be critical for an actor involved in performing one or more actions during a surgical procedure (e.g., by a surgeon). In one or more aspects, the structures are predicted dynamically and substantially in real-time as the surgical data is being captured and analyzed by technical solutions described herein. A predicted structure can be an anatomical structure, a surgical instrument, etc.

In some instances, a computer-assisted surgical (CAS) system is provided that uses one or more machine-learning models, trained with surgical data, to augment environmental data directly sensed by an actor involved in performing one or more actions during a surgical procedure (e.g., a surgeon). Such augmentation of perception and action can increase action precision, optimize ergonomics, improve action efficacy, enhance patient safety, and improve the standard of the surgical process.

The surgical data provided to train the machine-learning models can include data captured during a surgical procedure, as well as simulated data. The surgical data can include time-varying image data (e.g., a simulated/real video stream from different types of cameras) corresponding to a surgical environment. The surgical data can also include other types of data streams, such as audio, radio frequency identifier (RFID), text, robotic sensors, other signals, etc. The machine learning models are trained to predict and identify, in the surgical data, "structures" including particular tools, anatomic objects, actions being performed in the simulated/real surgical stages. In one or more aspects, the machine-learning models are trained to define one or more parameters of the models so as to learn how to transform new input data (that the models are not trained on) to identify one or more structures. During the training, the models are input one or more data streams that may be augmented with data indicating the structures in the data streams, such as indicated by metadata and/or image-segmentation data associated with the input data. The data used during training can also include temporal sequences of one or more input data.

In one or more aspects, the simulated data can be generated to include image data (e.g., which can include time-series image data or video data and can be generated in any wavelength of sensitivity) that is associated with variable perspectives, camera poses, lighting (e.g., intensity, hue, etc.) and/or motion of imaged objects (e.g., tools). In some instances, multiple data sets can be generated—each of which corresponds to the same imaged virtual scene but varies with respect to perspective, camera pose, lighting, and/or motion of imaged objects, or varies with respect to the modality used for sensing, e.g., red-green-blue (RGB) images or depth or temperature. In some instances, each of the multiple data sets corresponds to a different imaged virtual scene and further varies with respect to perspective, camera pose, lighting, and/or motion of imaged objects.

The machine-learning models can include a fully convolutional network adaptation (FCN) and/or conditional generative adversarial network model configured with one or more hyperparameters to perform image segmentation into classes. For example, the machine-learning models (e.g., the fully convolutional network adaptation) can be configured to perform supervised, self-supervised or semi-supervised semantic segmentation in multiple classes—each of which corresponding to a particular surgical instrument, anatomical body part (e.g., generally or in a particular state), and/or environment. Alternatively, or in addition, the machine-learning model (e.g., the conditional generative adversarial network model) can be configured to perform unsupervised domain adaptation to translate simulated images to semantic instrument segmentations. As a further example, the machine-learning models can include one or more transformer-based networks. It is understood that other types of machine-learning models or combinations thereof can be used in one or more aspects. Machine-learning models can be collectively managed as a group, also referred to as an ensemble, where the machine-learning models are used together and may share feature spaces between elements of the models. As such, reference to a machine-learning model or machine-learning models herein may refer to a combination of multiple machine-learning models that are used together, such as operating on a same group of data.

Machine-learning models can also be further subdivided into multiple networks that have specific types of outputs, which may be individual parameters or multi-dimensional regions.

In one or more aspects, one or more machine-learning models are trained using multiple detectors that can operate on a shared set of input data and/or intermediate computed features. Further machine-learning refinements can be achieved by using one or more outputs of previously trained machine-learning networks. For example, semi-supervised learning can be used to initially train the one or more machine-learning models using partially annotated input data as a training dataset. A surgical workflow can include, for instance, surgical phases, steps, actions, and/or other such states/activities. Aspects further described herein with respect to surgical phase can be applied to other surgical workflow states/activities, such as surgical steps and/or actions. A surgical workflow and structure network learned as part of the one or more machine-learning models can be used to train and enhance one or more other networks. For example, feature space data from the surgical workflow and structure network can be fused with feature space data used for a region of interest proposal network. A proposed region of interest output of the region of interest proposal network can provide partial input to an image synthesis network. Thus, learning by multiple machine-learning models is chained to enhance detection and image adjustment using features related to surgical phase, anatomy, instruments, motion/depth, and multiple types of inputs, such as temporal, spatial, and sensor inputs.

The trained machine-learning model can then be used in real-time to process one or more data streams (e.g., video streams, audio streams, RFID data, etc.). The processing can include predicting and characterizing one or more structures within various instantaneous or block time periods. The structure(s) can then be used to identify the presence, position, and/or use of one or more features. Alternatively, or in addition, the structures can be used to identify a stage within a workflow (e.g., as represented via a surgical data structure), predict a future stage within a workflow, etc.

FIG. 1 shows a system 100 for predicting structures in surgical data using machine learning according to one or more aspects. System 100 uses data streams that are part of the surgical data to identify procedural states according to some aspects. System 100 includes a procedural control system 105 that collects image data and coordinates outputs responsive to predicted structures and states. The procedural control system 105 can include one or more devices (e.g., one or more user devices and/or servers) located within and/or associated with a surgical operating room and/or control center. System 100 further includes a machine-learning processing system 110 that processes the surgical data using a machine-learning model to identify a procedural state (also referred to as a phase or a stage), which is used to identify a corresponding output. It will be appreciated that machine-learning processing system 110 can include one or more devices (e.g., one or more servers), each of which can be configured to include part or all of one or more of the depicted components of the machine-learning processing system 110. In some instances, a part, or all of machine-learning processing system 110 is in the cloud and/or remote from an operating room and/or physical location corresponding to a part, or all of procedural control system 105. For example, the machine learning training system 125 can be a separate device, (e.g., server) that stores its output as the one or more trained machine learning models 130, which are accessible by the model execution system 140, separate from the machine learning training system 125. In other words, in some aspects, devices that "train" the models are separate from devices that "infer," i.e., perform real-time processing of surgical data using the trained models 130.

Machine-learning processing system 110 includes a data generator 115 configured to generate simulated surgical data, such as a set of virtual images, or record surgical data from ongoing procedures, to train a machine-learning model. Data generator 115 can access (read/write) a data store 120 with recorded data, including multiple images and/or multiple videos. The images and/or videos can include images and/or videos collected during one or more procedures (e.g., one or more surgical procedures). For example, the images and/or video may have been collected by a user device worn by a participant (e.g., surgeon, surgical nurse, anesthesiologist, etc.) during the surgery, and/or by a non-wearable imaging device located within an operating room.

Each of the images and/or videos included in the recorded data can be defined as a base image and can be associated with other data that characterizes an associated procedure and/or rendering specifications. For example, the other data can identify a type of procedure, a location of a procedure, one or more people involved in performing the procedure, and/or an outcome of the procedure. Alternatively, or in addition, the other data can indicate a stage of the procedure with which the image or video corresponds, rendering specification with which the image or video corresponds and/or a type of imaging device that captured the image or video (e.g., and/or, if the device is a wearable device, a role of a particular person wearing the device, etc.). Further, the other data can include image-segmentation data that identifies and/or characterizes one or more objects (e.g., tools, anatomical objects, etc.) that are depicted in the image or video. The characterization can indicate the position, orientation, or pose of the object in the image. For example, the characterization can indicate a set of pixels that correspond to the object and/or a state of the object resulting from a past or current user handling.

Data generator 115 identifies one or more sets of rendering specifications for the set of virtual images. An identification is made as to which rendering specifications are to be specifically fixed and/or varied. Alternatively, or in addition, the rendering specifications that are to be fixed (or varied) are predefined. The identification can be made based on, for example, input from a client device, a distribution of one or more rendering specifications across the base images and/or videos, and/or a distribution of one or more rendering specifications across other image data. For example, if a particular specification is substantially constant across a sizable data set, the data generator 115 defines a fixed corresponding value for the specification. As another example, if rendering-specification values from at least a predetermined amount of data span across a range, the data generator 115 define the rendering specifications based on the range (e.g., to span the range or to span another range that is mathematically related to the range of distribution of the values).

A set of rendering specifications can be defined to include discrete or continuous (finely quantized) values. A set of rendering specifications can be defined by a distribution, such that specific values are to be selected by sampling from the distribution using random or biased processes.

One or more sets of rendering specifications can be defined independently or in a relational manner. For example, if the data generator 115 identifies five values for a first rendering specification and four values for a second rendering specification, the one or more sets of rendering specifications can be defined to include twenty combinations of the rendering specifications or fewer (e.g., if one of the second rendering specifications is only to be used in combination with an incomplete subset of the first rendering specification values or the converse). In some instances, different rendering specifications can be identified for different procedural phases and/or other metadata parameters (e.g., procedural types, procedural locations, etc.).

Using the rendering specifications and base image data, the data generator 115 generates simulated surgical data (e.g., a set of virtual images), which is stored at the data store 120. For example, a three-dimensional model of an environment and/or one or more objects can be generated using the base image data. Virtual image data can be generated using the model to determine—given a set of particular rendering specifications (e.g., background lighting intensity, perspective, zoom, etc.) and other procedure-associated metadata (e.g., a type of procedure, a procedural state, a type of imaging device, etc.). The generation can include, for example, performing one or more transformations, translations, and/or zoom operations. The generation can further include adjusting the overall intensity of pixel values and/or transforming RGB values to achieve particular color-specific specifications.

A machine learning training system 125 uses the recorded data in the data store 120, which can include the simulated surgical data (e.g., set of virtual images) and actual surgical data to train one or more machine-learning models. The machine-learning models can be defined based on a type of model and a set of hyperparameters (e.g., defined based on input from a client device). The machine-learning models can be configured based on a set of parameters that can be dynamically defined based on (e.g., continuous or repeated) training (i.e., learning, parameter tuning). Machine learning training system 125 can use one or more optimization algorithms to define the set of parameters to minimize or maximize one or more loss functions. The set of (learned) parameters can be stored as a trained machine-learning model data structure 130, which can also include one or more non-learnable variables (e.g., hyperparameters and/or model definitions).

A model execution system 140 can access the machine-learning model data structure 130 and accordingly configure a machine-learning model for inference (i.e., prediction). The machine-learning model can include, for example, a fully convolutional network adaptation, an adversarial network model, or other types of models as indicated in data structure 130. The machine-learning model can be configured in accordance with one or more hyperparameters and the set of learned parameters.

The machine-learning model, during execution, receives, as input, surgical data to be processed and generate an inference according to the training. For example, the surgical data can include data streams (e.g., an array of intensity, depth, and/or RGB values) for a single image or for each of a set of frames representing a temporal window of fixed or variable length in a video. The surgical data that is input can be received from a real-time data collection system 145, which can include one or more devices located within an operating room and/or streaming live imaging data collected during the performance of a procedure. The surgical data can include additional data streams such as audio data, RFID data, textual data, measurements from one or more instruments/sensors, etc., that can represent stimuli/procedural state from the operating room. The different inputs from different devices/sensors are synchronized before inputting in the model.

The machine-learning model analyzes the surgical data, and in one or more aspects, predicts and/or characterizes structures included in the visual data from the surgical data. The visual data can include image and/or video data in the surgical data. The prediction and/or characterization of the structures can include segmenting the visual data or predicting the localization of the structures with a probabilistic heatmap. In some instances, the machine-learning model includes or is associated with a preprocessing or augmentation (e.g., intensity normalization, resizing, cropping etc.) that is performed prior to segmenting the visual data. An output of the machine-learning model can include image-segmentation or probabilistic heatmap data that indicates which (if any) of a defined set of structures are predicted within the visual data, a location and/or position and/or pose of the structure(s) within the image data, and/or state of the structure(s). The location can be a set of coordinates in the image data. For example, the coordinates can provide a bounding box. Alternatively, the coordinates provide boundaries that surround the structure(s) being predicted.

A state detector 150 can use the output from the execution of the machine-learning model to identify a state within a surgical procedure ("procedure"). A procedural tracking data structure can identify a set of potential states that can correspond to part of a performance of a specific type of procedure. Different procedural data structures (e.g., and different machine-learning-model parameters and/or hyperparameters) may be associated with different types of procedures. The data structure can include a set of nodes, with each node corresponding to a potential state. The data structure can include directional connections between nodes that indicate (via the direction) an expected order during which the states will be encountered throughout an iteration of the procedure. The data structure may include one or more branching nodes that feed to multiple next nodes and/or can include one or more points of divergence and/or convergence between the nodes. In some instances, a procedural state indicates a surgical action that is being performed or has been performed and/or indicates a combination of actions that have been performed. A "surgical action" can include an operation such as, an incision, a compression, a stapling, a clipping, a suturing, a cauterization, a sealing, or any other such actions performed to complete a step/phase in the surgical procedure. In some instances, a procedural state relates to a biological state of a patient undergoing a surgical procedure. For example, the biological state can indicate a complication (e.g., blood clots, clogged arteries/veins, etc.), pre-condition (e.g., lesions, polyps, etc.).

Each node within the data structure can identify one or more characteristics of the state. The characteristics can include visual characteristics. In some instances, the node identifies one or more tools that are typically in use or availed for use (e.g., on a tool try) during the state, one or more roles of people who are typically performing a surgical task, a typical type of movement (e.g., of a hand or tool), etc. Thus, state detector 150 can use the segmented data generated by model execution system 140 that indicates the presence and/or characteristics of particular objects within a field of view to identify an estimated node to which the real image data corresponds. Identification of the node (and/or state) can further be based upon previously detected states for a given procedural iteration and/or other detected input (e.g., verbal audio data that includes person-to-person requests or comments, explicit identifications of a current or past state, information requests, etc.).

An output generator 160 can use the state to generate an output. Output generator 160 can include an alert generator 165 that generates and/or retrieves information associated with the state and/or potential next events. For example, the information can include details as to warnings and/or advice corresponding to current or anticipated procedural actions. The information can further include one or more events for which to monitor. The information can identify the next recommended action.

The user feedback can be transmitted to an alert output system 170, which can cause the user feedback to be output via a user device and/or other devices that is (for example) located within the operating room or control center. The user feedback can include a visual, audio, tactile, or haptic output that is indicative of the information. The user feedback can facilitate alerting an operator, for example surgeon, or any another user of the system.

Output generator 160 can also include an augmentor 175 that generates or retrieves one or more graphics and/or text to be visually presented on (e.g., overlaid on) or near (e.g., presented underneath or adjacent to or on separate screen) real-time capture of a procedure. Augmentor 175 can further identify where the graphics and/or text are to be presented (e.g., within a specified size of a display). In some instances, a defined part of a field of view is designated as being a display portion to include augmented data. In some instances, the position of the graphics and/or text is defined so as not to obscure the view of an important part of an environment for the surgery and/or to overlay particular graphics (e.g., of a tool) with the corresponding real-world representation.

Augmentor 175 can send the graphics and/or text and/or any positioning information to an augmented reality device 180, which can integrate the graphics and/or text with a user's environment in real-time as an augmented visualization. Augmented reality device 180 can include a pair of goggles that can be worn by a person participating in part of the procedure. It will be appreciated that, in some instances, the augmented display can be presented at a non-wearable user device, such as at a computer or tablet. The augmented reality device 180 can present the graphics and/or text at a position as identified by augmentor 175 and/or at a pre-defined position. Thus, a user can maintain a real-time view of procedural operations and further view pertinent state-related information.

Figure 2:
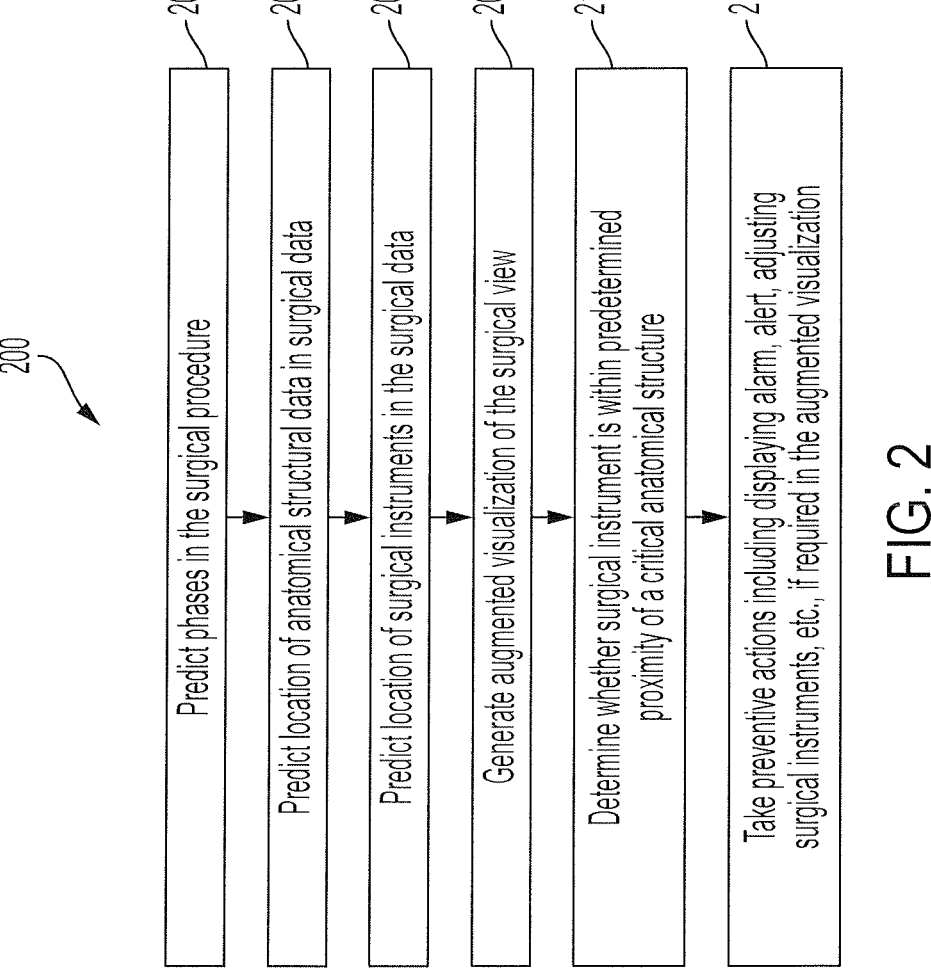
FIG. 2 depicts a flowchart of a method for predicting structures in surgical data using machine learning according to one or more aspects.

FIG. 2 depicts a flowchart of a method for predicting structures in surgical data using machine learning according to one or more aspects. The method 200 can be executed by the system 100 as a computer-implemented method.

The method 200 includes training and using (inference phase) a first machine learning model 350 to predict surgical phases being performed in the procedure from the surgical data, at block 202. The phases can be determined using "operative workflow analysis"—systematically deconstructing operations into steps and phases using machine learning. A "step" refers to the completion of a named surgical objective (e.g. hemostasis), while a "phase" represents a surgical event that is composed of a series of steps (e.g. closure). During each step, certain surgical instruments (e.g. forceps) are used to achieve a specific objective, and there is the potential for technical error (lapses in operative technique). Machine learning based recognition of these elements allows surgical workflow analysis to be generated automatically. Artificial deep neural networks (DNN), or other types of machine learning models, can be used to achieve automatic accurate phase and instrument recognition in the surgical procedures, such as cataract surgery, laparoscopic cholecystectomy, endoscopic endonasal transsphenoidal approach (eTSA) to resection of pituitary adenomas, or any other surgical procedure.

In one or more aspects, separate instances of the machine learning model are trained for respective types of procedures. For example, a machine learning model-1 is trained to predict phases in knee arthroscopy; a machine learning model-2 is trained to predict phases in laparoscopic removal of a gallbladder; a machine learning model-3 is trained to predict phases in endoscopic mucosal resection, and so on. Because each procedure can have specific phases (e.g., the sequence of operations) and specific attributes (e.g., anatomical features, instruments, etc.), respective machine learning models are trained to predict and identify the phases of the procedures. It is understood that the technical solutions described herein are not limited to a particular type of surgical procedure unless explicitly indicated. As such, "surgical procedure" or "procedure" can be anyone or more surgeries performed, and not limited to the above-listed examples.

The machine learning model includes a feature encoder to predict features from the surgical data for the procedure. The feature encoder can be based on one or more artificial neural networks, such as convolutional neural network (CNN), recurrent neural network (RNN), feature pyramid network (FPN), transformer networks, or any other type of neural network or a combination thereof. The feature encoder can use a known technique, supervised, self-supervised or unsupervised (e.g., autoencoder), to learn efficient data "codings" in the surgical data. The "coding" maps an input data to a feature space, which can be used by feature decoders to perform semantic analysis of the surgical data. In one or more aspects, the machine learning model includes task-specific decoders that predict instruments being used at an instance in the surgical data based on the predicted features. Additionally, the machine learning model includes task-specific decoders that predict the surgical phases in the surgical data based on the predicted features.

Figure 3:
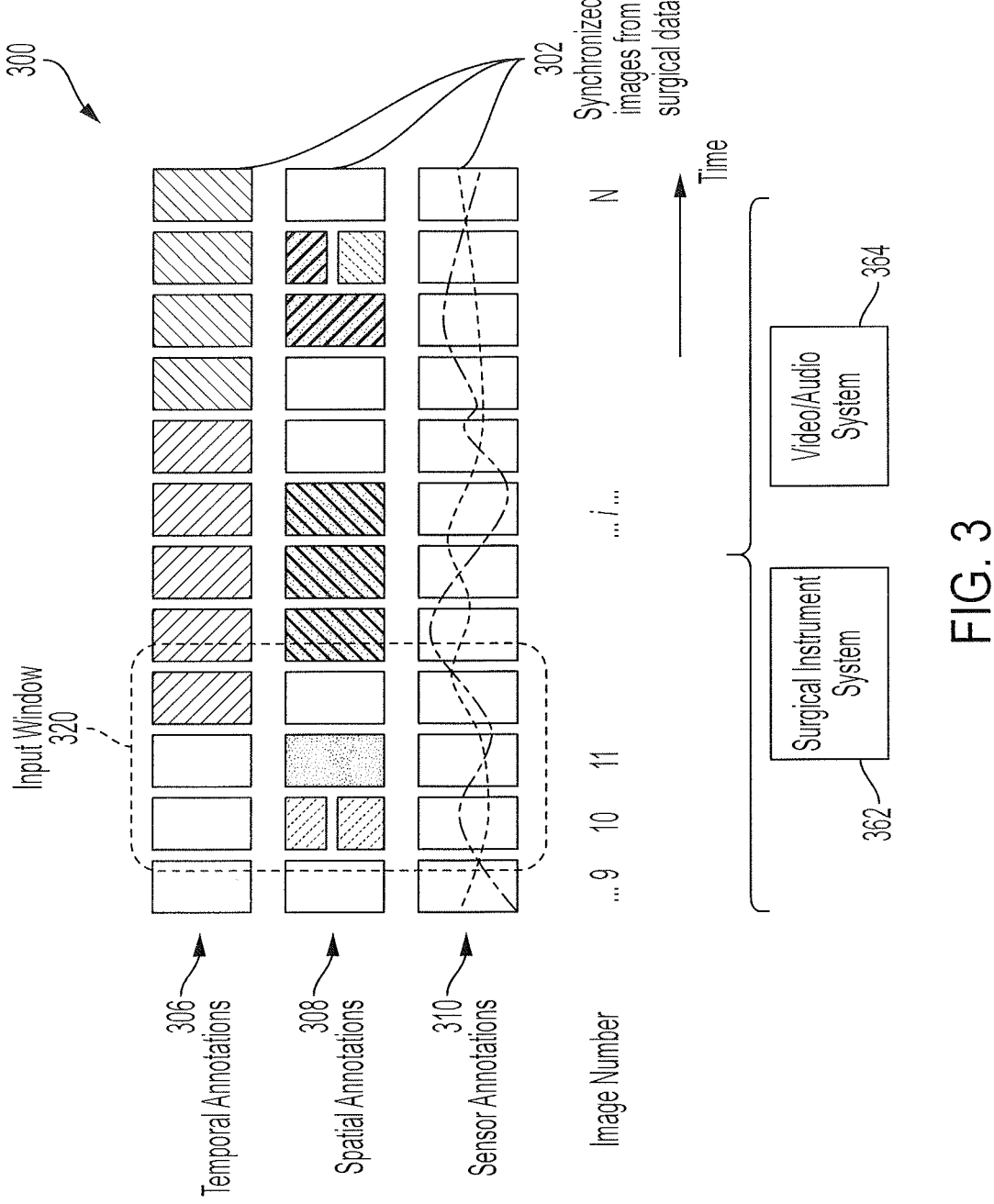
FIG. 3 depicts a visualization of surgical data being used for training a machine learning model according to one or more aspects.

It should be noted that the machine learning model operates on the surgical data per frame, but can use information from previous frame, or a window of previous frames. FIG. 3 depicts a visualization of surgical data being used for training a machine learning model according to one or more aspects. The depicted example surgical data 300 includes video data, i.e., a set of N images 302. The N images may be sequential in some examples. Alternatively, or in addition, the N images can be arbitrarily sampled temporal set of frames/sensor/data information. The audio-visual data can be captured using an audio/video system 364. The audio/video system includes one or more video capture devices that can include cameras placed in the surgical room to capture events surrounding (i.e., outside) the patient. The audio/video system includes cameras that are passed inside (e.g., endoscopic cameras) the patient to capture endoscopic data. The endoscopic data provides video, images of the surgical procedure that are used to identify surgical phases, structures, such as anatomical structures, surgical instruments, etc. For training the machine learning model, images 302, and other inputs are annotated. The annotations can include temporal annotations 306 that identify a surgical phase to which an image belongs or tracking information for different structures. Accordingly, a particular set or subset of sequential images 302 represents a surgical phase, or tracking state. The subset of sequential images 302 can include one or more images.

Further, the annotations include spatial annotations 308 that identify one or more objects in the images 302. For example, the spatial annotations 308 can specify one or more regions of an image and identify respective objects in the regions. Further, an image can include sensor annotations 310 that include values of one or more sensor measurements at the time the image was captured. The sensor measurements can be from sensors associated with the patient, such as oxygen level, blood pressure, heart rate, etc. Alternatively, or in addition, the sensor measurements can be associated with one or more components being used in the surgical procedure, such as a brightness level of an endoscope, a fluid level in a tank, energy output from a generator etc. Sensor measures can also come from real-time robotic systems indicating surgical activations or position or pose information about instruments. Other types of annotations can be used to train the machine learning model in other aspects.

In one or more examples, the sensor information can be received from a surgical instrumentation system 362. The surgical instrumentation system can include electrical energy sensors, electrical impedance sensors, force sensors, bubble and occlusion sensors, and various other types of sensors. The electrical energy sensors can measure and indicate an amount of electrical energy applied to one or more surgical instruments being used for the surgical procedure. The impedance sensors can indicate an amount of impedance measured by the surgical instruments, for example, from the tissue being operated upon. The force sensors can indicate an amount of force being applied by the surgical instruments. Measurements from various other sensors, such as position sensors, pressure sensors, flow meters, can also be input. Such instrument data is used to train machine learning algorithms to determine one or more actions being performed during the surgical procedure. For example, vessel sealing, clipping, or any other manipulations of the surgical instruments can be detected based on the instrument data using machine learning.

The machine learning model can take into consideration one or more temporal inputs, such as sensor information, acoustic information, along with spatial annotations associated with images 302 when detecting features in the surgical data 300. A set of such temporally synchronized inputs from the surgical data 300 that are analyzed together by the machine learning model can be referred to as an "input window" 320. The machine learning model, during inference, operates on the input window 320 to predict a surgical phase represented by the images in the input window 320 (block 202). Each image 302 in the input window 320 is associated with synchronized temporal and spatial annotations, such as measurements at a particular timepoint including sensor information, acoustic information, and other information. The images 302 that are used by the machine learning models may or may not be sequential.

The input from the surgical instrumentation system 362 and the audio/video system 364 is temporally synchronized, in one or more examples. A set of such temporally synchronized inputs from the surgical data 300 that are analyzed together by the machine learning model can be referred to as an "input window" 320. The machine learning model, during inference, operates on the input window 320 to predict a surgical phase represented by the images in the input window 320 (block 202). Each input window 320 can include multiple data streams from different sources: one or more images 302 (or video) synchronized temporal and spatial data, such as measurements including sensor measurements, acoustic information, and other information that is used by the machine learning model(s) to detect/predict one or more aspects autonomously.

Temporally synchronizing the video data from the surgical instrumentation system 362 and audio/video system 364.

The synchronization includes identifying image(s) 302 from the video data associated with a manipulation of a surgical instrument at a timepoint t1. Alternatively, the synchronization includes identifying the surgical instrumentation data associated with an image 302 at a timepoint t2. In one or more examples, the surgical instrumentation system 362 and the audio/video system 364 operate using synchronized clocks, and include timestamps from such clocks when the respective data is recorded. The timestamps from the synchronized clocks can be used to synchronize the two data streams. Alternatively, the surgical instrumentation system 362 and the audio/video system 364 operate on a single clock, and the timestamps can be used to synchronize the respective data streams.

Figure 4:
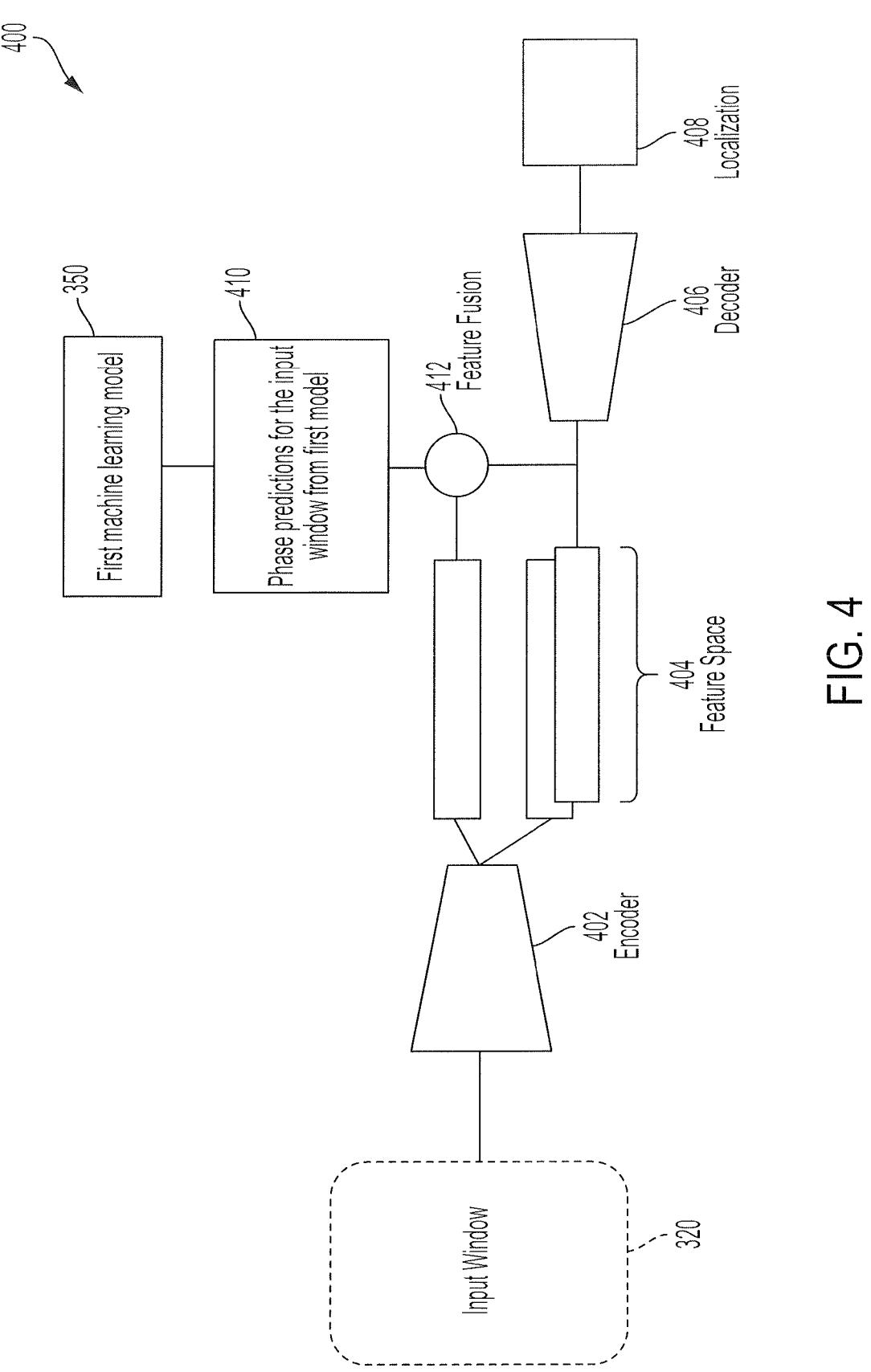
FIG. 4 depicts a machine learning model used to predict anatomical structures in the surgical data according to one or more aspects.

Further, the method 200 of FIG. 2 includes training and using (inference phase) a second machine learning model to predict location(s) of anatomical structural data in the surgical data in the input window 320, at block 204. FIG. 4 depicts a machine learning model 400 used to predict anatomical structures in the surgical data according to one or more aspects. The second machine learning model 400 can be a computer vision model. The second machine learning model 400 can be a combination of one or more artificial neural networks, such as encoders, Recurrent Neural Networks (RNN, e.g. LSTM, GRU etc.), CNNs, Temporal Convolutional Neural Networks (TCNs), decoders, Transformers, other deep neural networks, etc. For example, the second machine learning model 400 includes an encoder 402 that is trained using weak labels (such as lines, ellipses, local heatmaps or rectangles) or full labels (segmentation masks, heatmaps) to predict (i.e., detect and identify) to predict features in the surgical data. In some cases, full labels can be automatically generated from weak labels by using trained machine learning models). The encoder or backbone 402 can be implemented using architectures such as ResNet, VGG, or other such neural network architectures. During training, the encoder 402 is trained using input windows 320 that includes images 302 that are annotated with the labels (weak or full).

The encoder 402 generates a feature space 404 from the input window 320. The feature space 404 includes the extracted features from the input window by the encoder 402. The features include one or more labels assigned by the encoder 402 to one or more portions of the surgical data in the input window 320.

The second machine learning model 400 further includes a decoder 406 that predicts and outputs anatomical localization 408 based on the feature space 404. The anatomical localization 408 provides locations, e.g., coordinates, heatmaps, bounding boxes, boundaries, masks, etc., of one or more anatomical structures identified in the input window 320. A "location" of a detected feature, such as an anatomical structure, surgical instrument, etc., can be specified as multiple sets of coordinates (e.g., polygon), a single set of coordinates (e.g., centroid), or any other such manner without limiting the technical features described herein. Anatomical structures that are identified can include organs, arteries, implants, surgical artifacts (e.g., staples, stitches, etc.), etc. Further yet, based on the type of surgical procedure being performed, one or more of the predicted anatomical structures can be identified as critical structures for the success of the procedure. The anatomical localization 408, in one or more aspects, is limited to the spatial domain (e.g., bounding box, heatmap, segmentation mask) of the critical structures but uses temporal annotations 306 to enhance temporal consistency of the predictions. The temporal annotations 306 can be based on sensor measurements, acoustic information, and other such data that is captured at the time of capturing the respective images 302.

In one or more aspects, the decoder 406 further uses information output by the first machine learning model 350, including the phase data. The phase information is injected as a prior during training the second machine learning model 400. The temporal information that is provided by the phase information is used to refine confidence of the anatomy prediction in one or more aspects. In one or more aspects, the temporal information is fused (412) with the feature space 404, and the resulting fused information is used by the decoder 406 to output the anatomical localization 408.

The feature fusion 412 can be based on transform-domain image fusion algorithms to implement an image fusion neural network (IFNN). For example, an initial number of layers in the IFNN extract salient features from the temporal information output by the first model and the feature space 404. Further, the extracted features are fused by an appropriate fusion rule (e.g., elementwise-max, elementwise-min, elementwise-mean, etc.) or a more complex learning-based neural network module designed to learn to weight and fuse input data (e.g. using attention modules). The fused features are reconstructed by subsequent layers of the IFNN to produce input data, such as an informative fusion image, for the decoder 406 to analyze. Other techniques for fusing the features can be used in other aspects.

The anatomical localization 408 can further include a measure of the uncertainty of the processing, i.e., how confident the second machine learning model 400 is that the data points resulting from the processing are correct. The measure represents a confidence score of the second machine learning model's outputs. The confidence score is a measure of the reliability of the prediction from the second machine learning model 400. For example, a confidence score of 95 percent or 0.95 means that there is a probability of at least 95 percent that the prediction is reliable. The confidence score can be computed as a distance transform from the central axis of structure (i.e. how close from the centroid of the structure) to attenuate predictions near the boundaries. The confidence score can also be computed as a probabilistic formulation of the second machine learning model 400 (e.g., Bayesian deep learning, probabilistic outputs like SoftMax or sigmoid functions, etc.). In some aspects, the confidence scores for various predictions are scaled and/or normalized within a certain range, e.g., [0, 1].

Referring to the flowchart in FIG. 2, the method 200 further includes identifying localization of surgical instruments in the field of view, i.e., the input window 320, at block 206. In one or more aspects, the first machine learning model 350 that predicts the phase information also outputs the localization of the surgical instruments. Alternatively, another machine learning model (a third machine learning model) is trained and used to predict the surgical instruments in the surgical data 300. The third machine learning model can have the same structure as the second machine learning model 400 and use feature fusion 412 to take advantage of the phase information predicted by the first machine learning model 350. In comparison to the anatomical structural predictions made by the second machine learning model 400, the third machine learning model is trained to predict and identify surgical instruments in the images 302 in the input window 320.

The localization output by the third machine learning model provides locations of the surgical instrument(s) in the images 302. For example, the localization of the surgical instrument(s) can include a bounding box, a medial axis, a segmentation mask, and/or any other marker or key point identifying the location of the surgical instrument(s). The localization can be represented as coordinates in the images 302 that map to pixels depicting the surgical instrument(s) in the images 302.

The method 200 further includes generating an augmented visualization of the surgical view using the data points obtained from the processing, at block 208. The augmented visualization can include, for example, displaying segmentation masks or probability maps over instruments, anatomical structures, or specific points of interest in the surgical data 300.

Figure 5:
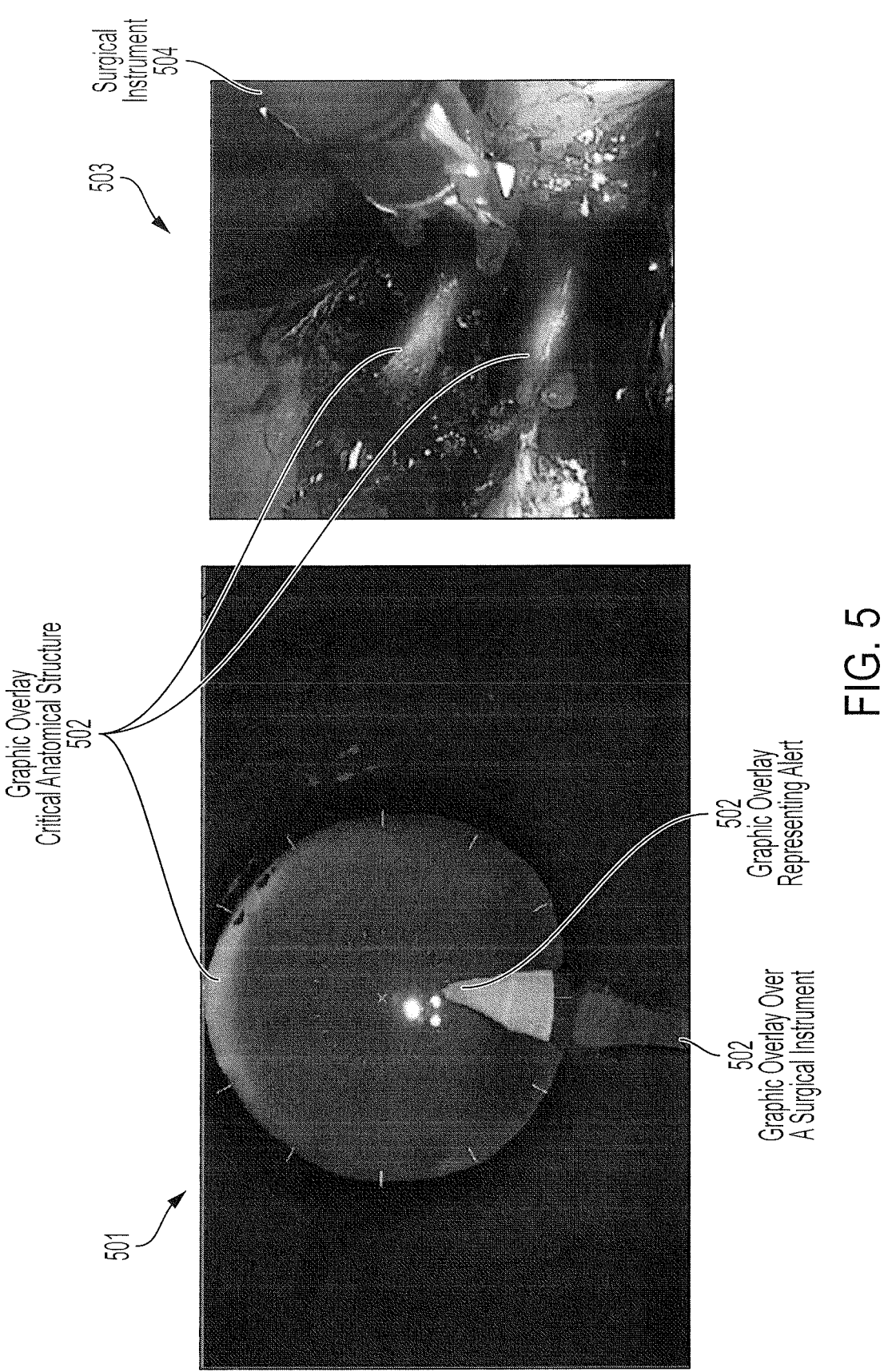
FIG. 5 depicts example augmented visualizations of surgical views generated according to one or more aspects.

FIG. 5 depicts example augmented visualizations of surgical views generated according to one or more aspects. It is understood that those shown are examples and that various other augmented visualizations can be generated in other aspects. Images captured during an eye surgery are depicted in the augmented visualizations 501, 503. The augmented visualizations 501, 503 are from different phases in the surgical procedure, and accordingly, the anatomical structures, surgical instruments, and other details in the surgical view are different. Further, according to the phase of the surgical procedure, the critical anatomical structure also changes. In the augmented visualization 501, the iris and a specific portion of the iris that is to be operated on are marked as critical anatomical structures using a graphical overlay 502. The sclera, which is also seen, is not marked. In the augmented visualization 503, the internals of the eye are seen, such as ciliary muscle, vitreous gel, fovea, choroid, macula, retina, etc. Among the anatomical structures that are seen, the critical anatomical structures that are to be operated upon are marked using graphical overlays 502.

A user can configure which predictions from the machine learning system 100 are to be displayed by the augmentor 175. For example, the user can configure to display overlays 502 on a partial set of the predictions, with the other predictions not being marked in the augmented reality device 180. Further, the user can configure one or more thresholds that determine when to generate an alert based on one or more metrics (e.g., certainty, accuracy, etc.) associated with the predictions. The user can further configure the attributes to be used generate the user feedback, such as the overlays 502. For example, the color, the border, the transparency, the priority, the audible sound, and other such attributes of the user feedback can be configured.

"Critical anatomical structures" can be specific to the type of surgical procedure being performed and identified automatically. Additionally, the surgeon or any other user can configure the system 100 to identify particular anatomical structures as critical for a particular patient. The selected anatomical structures are critical to the success of the surgical procedure, such as anatomical landmarks (e.g., Calot triangle, Angle of His, etc.) that need to be identified during the procedure or those resulting from a previous surgical task or procedure (e.g., stapled or sutured tissue, clips, etc.).

Further, the augmented visualizations 501, 503 can mark surgical instruments in the surgical data 300 using graphical overlays 502. The surgical instruments are identified by the machine learning model, as described herein. In one or more aspects, a surgical instrument is only marked if it is within a predetermined threshold proximity of an anatomical structure. In some aspects, the surgical instrument is only marked if it is within a predetermined threshold proximity of a critical anatomical structure. In some aspects, a surgical instrument is always marked with a graphical overlay 502, but the opacity (or any other attribute) of the graphical overlay 502 is varied based on an importance-score associated with the surgical instrument. The importance-score can be based on the surgical procedure being performed. For example, during a knee-arthroscopy for a meniscus injury, an arthroscopic scissor, a suture cutter, a meniscus retractor, or other such surgical instruments may have a larger importance-score compared to an arthroscopic punch, a biter, etc. The importance-scores for the surgical instruments can be configured by the operator, and can be set by default based on the type of the surgical procedure being performed. The graphical overlays 502 for other detected features, such as anatomical structures, are also adjusted in the same manner as those for a surgical instrument.

Here, "marking" an anatomical structure, surgical instrument, or other features in the surgical data includes visually highlighting that feature for the surgeon or any other user by using a graphical overlay 502. The graphical overlay 502 can include a heatmap, a contour, a bounding box, a mask, a highlight, or any other such visualization that is overlaid on the images 302 from the surgical data 300 that are being displayed to the user. The examples in FIG. 5 depict using masks and heatmaps as the graphical overlays 502. However, different techniques can be used in other aspects.

Various visual attributes of the graphical overlay 502, such as colors, transparency, visual-pattern, line thickness, etc., can be adjusted. In addition, the graphic overlay 502 can include annotations. The annotation can identify the anatomical structure(s), objects that are marked using the graphic overlay 502 based on the prediction by the second machine learning model 400. Additionally, the annotation can include a note, a sensor measurement, or other such information for the user.

In one or more aspects, a user can adjust the attributes of the graphic overlays 502. For example, the user can select a type of highlighting, a color, a line thickness, a transparency, a shading pattern, a label, an outline, or any other such attributes to be used to generate and display the graphical overlay on the images 302. In some aspects, the color and/or transparency of the graphical overlay 502 is modulated based on the confidence score associated with the prediction, i.e., identification of the underlying anatomical structure or surgical instrument by the machine learning model(s).

In some aspects, the graphical overlays 502 are used to provide a critical structure warning. Referring to the flow-chart, the method 200 includes predicting whether the surgeon is operating within a predetermined proximity of a critical anatomical structure, at block 210. Such a determination can be made based on a surgical instrument being within a predetermined proximity (e.g., 0.5 millimeters, 0.2 millimeters, etc.) of a critical anatomical structure. If a surgical instrument is determined to be within the predetermined threshold of a critical anatomical structure, one or more preventive measures are taken, at block 212.

The preventive measures can include generating and displaying a graphical overlay 502 on the surgical view to indicate a user feedback (e.g., warning/alert, annotation, notification etc.). Alternatively, or in addition, preventive measures can be integrated into a robotic workflow in response to the predictions described herein. For example, operating parameters of one or more surgical instruments are adjusted (e.g., limited/restrained) to prevent injury to the patient. For example, during a ureteroscopy, to prevent injury to ureters and/or pulmonary vasculature, the energy level of monopolar instruments is reduced when dissecting in the proximity of neurovascular bundles. Additional preventive measures can also be taken in other aspects by adjusting operating parameters, such as, speed, rotations, vibrations, energy, etc., that can facilitate prohibiting (or enhancing) one or more actions being performed using the surgical instrument.

Aspects of the technical solutions described herein improve surgical procedures by improving the safety of the procedures. Further, the technical solutions described herein facilitate improvements to computing technology, particularly computing techniques used during a surgical procedure. Aspects of the technical solutions described herein facilitate one or more machine learning models, such as computer vision models, to process images obtained from a live video feed of the surgical procedure in real-time using spatio-temporal information. The machine learning models using techniques such as neural networks to use information from the live video feed and (if available) robotic sensor platform to predict one or more features, such as anatomical structures, surgical instruments, in an input window of the live video feed, and further refine the predictions using additional machine learning models that can predict a phase of the surgical procedure. The additional machine learning models are trained to identify the surgical phase(s) of the procedure and instruments in the field of view by learning from raw image data and instrument markers (bounding boxes, lines, key points, etc.). When in a robotic procedure, the computer vision models can also accept sensor information (e.g., instruments enabled, mounted, etc.) to improve the predictions. Computer Vision models that predict instruments and critical anatomical structures use temporal information from the phase prediction models to improve the confidence of the predictions in real-time.

The predictions and the corresponding confidence scores are used to generate and display graphical overlays to the surgeon and/or other users in an augmented visualization of the surgical view. The graphical overlays can mark critical anatomical structures, surgical instruments, surgical staples, scar tissue, results of previous surgical actions, etc. The graphical overlays can further show a relationship between the surgical instrument(s) and one or more anatomical structures in the surgical view and thus, guide the surgeon and other users during the surgery. The graphical overlays are adjusted according to the user's preferences and/or according to the confidence scores of the predictions.

By using machine learning models, and computing technology to predict and mark various features in the surgical view, in real-time, aspects of the technical solutions facilitate the surgeons to replace visualizations based on external contrast agents (e.g., Indocyanine green (ICG), Ethiodol, etc.) that have to be injected into the patient. Such contrast agents may not always be available to use because of the patient's preconditions or other factors. Accordingly, aspects of the technical solutions described herein provide a practical application in surgical procedures. In some aspects, the contrast agents can be used in addition to the technical solutions described herein. The operator, for example, the surgeon, can switch on/off either (or both) visualizations, the contrast agent based or the graphical overlays 502.

Further yet, aspects of the technical solutions described herein address technical challenges of predicting complex features in a live video feed of a surgical view in real-time. The technical challenges are addressed by using a combination of various machine learning techniques to analyze multiple images in the video feed. Additionally, technical challenges exist to determine relative depth in the images when determining if a surgical instrument is within a predetermined proximity of a critical anatomical structure. Aspects of the technical solutions described herein provide machine learning techniques that facilitate training a depth estimation algorithm to retrieve a proxy for relative depth in the images. Further yet, to address the technical challenge of real-time analysis and augmented visualization of the surgical view, aspects of the technical solutions described herein predict the present state of the surgical view at a constant frame rate and update the present state using the machine learning models at a predetermined frame rate.

Figure 6:
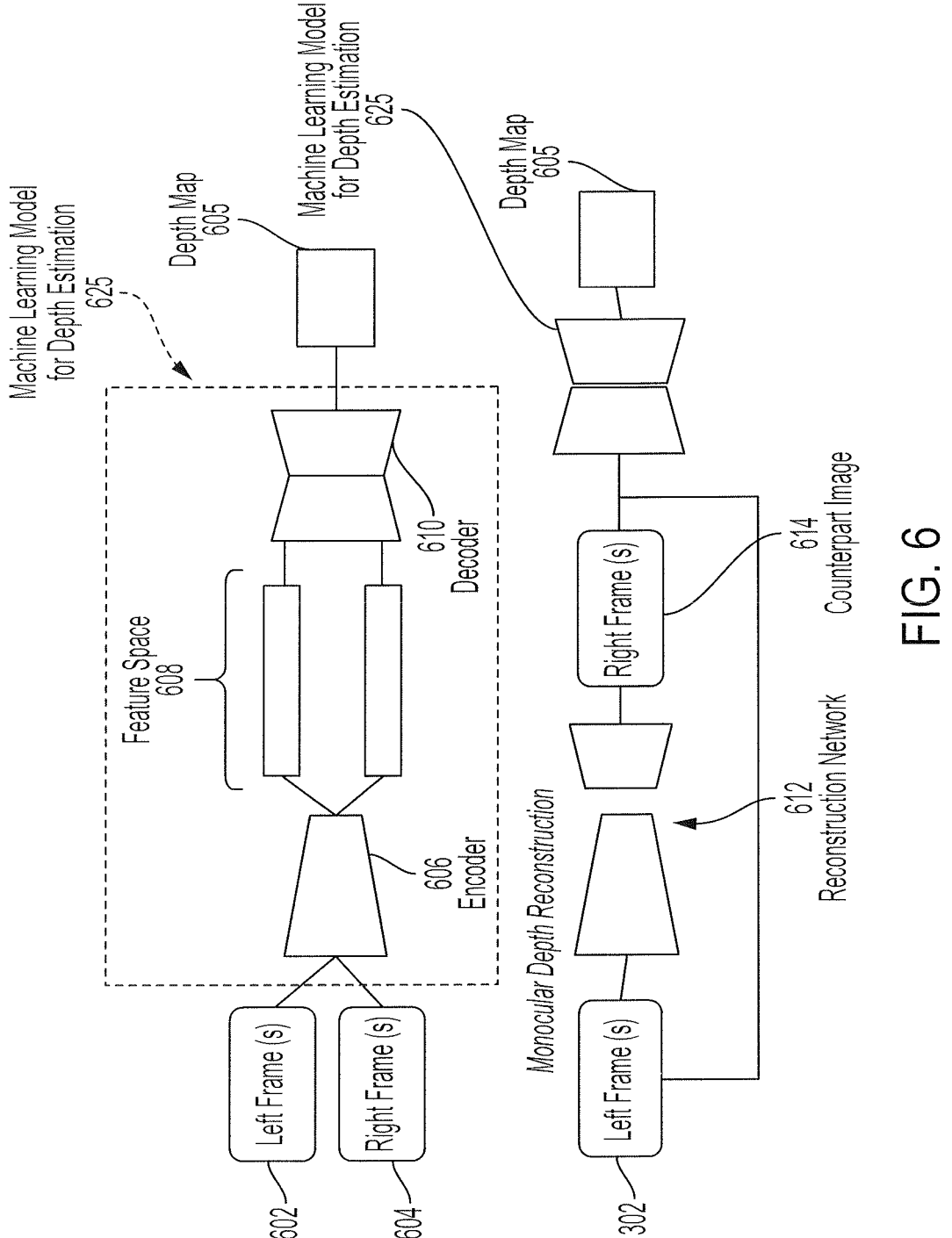
FIG. 6 depicts flow diagrams of depth estimation to retrieve a proxy for relative depth in the image.

FIG. 6 depicts flow diagrams of depth estimation to retrieve a proxy for relative depth in the image. The surgical procedure is being performed in 3D space, and hence, determining the proximity of surgical instruments and anatomical structures has to be performed in 3D space. However, the images 302 representing the surgical view are typically 2D. Therefore, a depth map of the surgical view has to be estimated based on the 2D images 302. Depth map calculation is a technical challenge in computing technology, as the calculation is expensive both in computing resources and in time. The aspects described herein address the technical challenge by using artificial neural network architecture that improves the runtime of calculating the depth map 605 in real-time. Further, the surgical view may be captured using a monocular image capture device (e.g., a single camera), which can adversely affect the estimation of the depth map. It should be noted that "depth map" can represent a disparity map, a stereo map, a distance map, or any other such data structures.

Aspects described herein address such technical challenges and provide a depth map for the surgical view in real-time.

FIG. 6 depicts training a machine learning model 625 used to estimate a depth map 605 of features seen in the surgical view. The machine learning model 625 is trained using a pair of stereo frames that are captured using a stereo image capture device (not shown). The stereo image capture device captures two frames, referred to herein as a left frame 602 and a right frame 604. It is understood that in other aspects, the stereo image capture can produce a top frame and a bottom frame or any other pair of images that capture a scene in the field of view of the stereo image capture device. The machine learning model 625 can also be trained to extract the depth map 605 using simulated data, for which exact depth is known and left/right projections can be taken. Additionally, models can also be trained with spatio-temporal information (e.g. using a window of frames/sensors and other inputs, like other models described herein).

The machine learning model is based on artificial neural network architecture. The neural network architecture includes an encoder 606 that is trained to extract features from the left frame 602 and the right frame 604, respectively. The features that are extracted into a feature space 608 can be based on filters, such as a Sobel filter, Prewitt operator, or other feature detection operators such as convolutional operators. Further, a decoder 610 determines the depth map 605 by matching the extracted features from the left frame 602 and the right frame 604 and computing the coordinates for each point in the scene based on the matched features. The encoder 606 and the decoder 610 each include RNN, CNN, Transformer, or other such neural networks. The depth map 605 provides the depth of each pixel in the scene captured by the stereo pair. During training, the ground truth of the depth map 605 is known, and accordingly, the encoder 606 and the decoder 610 are trained to find accurately matching features, and the depth of each pixel in the depth map 605 based on the matching features. The depth map 605 is an image with the same dimensions as the left frame 602 and the right frame 604, with the value of each pixel in the depth map 605 representing the depth of each of the points captured in the stereo pair.

During runtime, because a stereo image capture device can be absent, a monocular depth reconstruction is performed using the trained machine learning model 625. The images 302 that are captured are used to reconstruct corresponding counterpart images 614 using a reconstruction network (ResNet) 612. The original images 302 and the corresponding counterpart images 614 from the reconstruction network 612 are used as a stereo pair of images (left and right) that is input to the trained machine learning model 625 for estimating the depth map 605.

Figure 7:
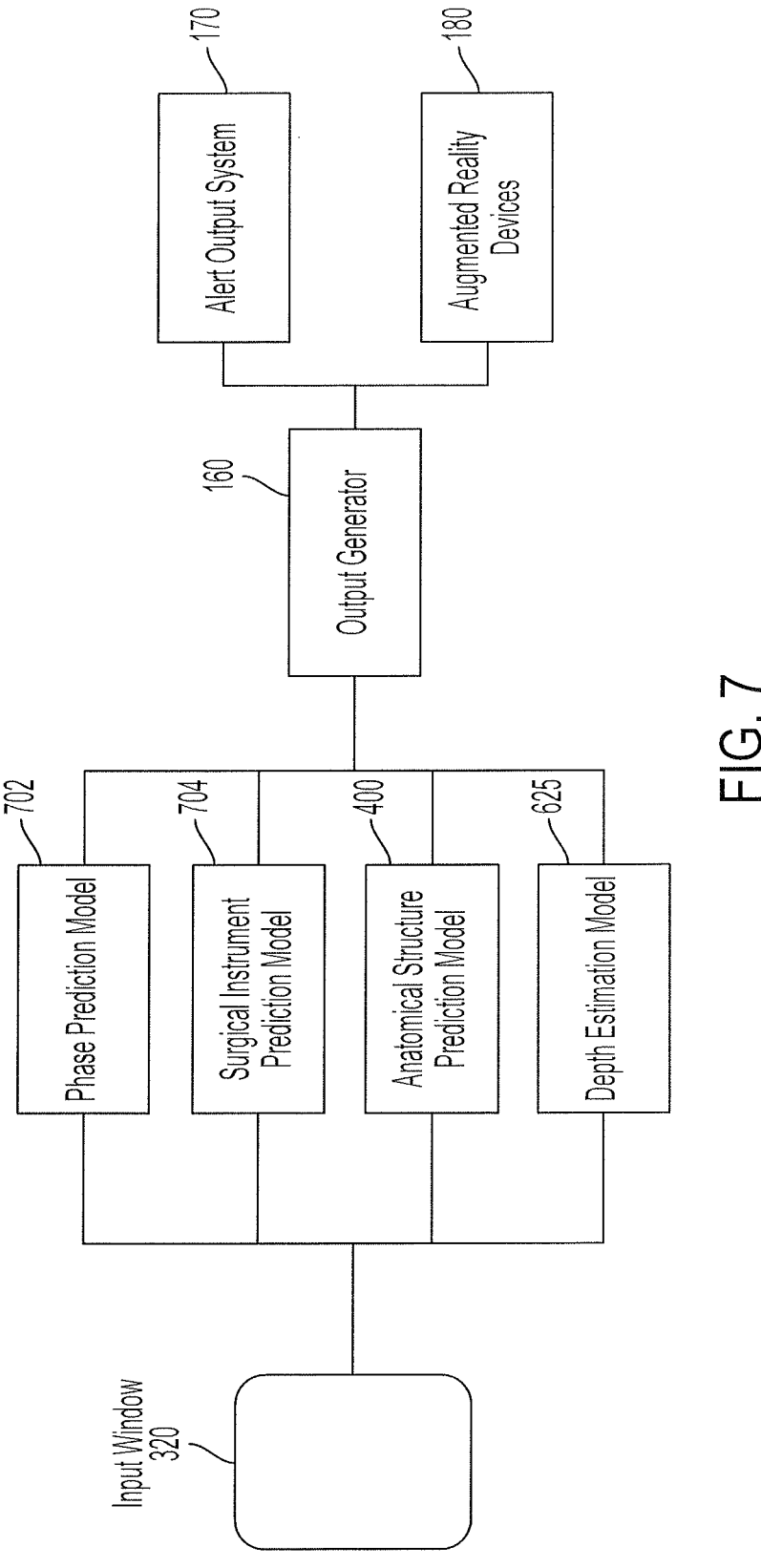
FIG. 7 depicts a flow diagram of automatic prediction of structures in surgical data using machine learning according to one or more aspects.

FIG. 7 depicts a flow diagram of automatic prediction of structures in surgical data using machine learning according to one or more aspects. The input window 320 is input to the model execution system 140 of FIG. 1 that uses a phase prediction model 702, which is a machine learning model, to predict the phase of the surgical procedure being performed. Further, the input window 320 is analyzed by the second machine learning model 400 to predict one or more anatomical structures. Further yet, surgical instruments in the surgical data are predicted using a surgical instrument prediction model 704, which is another machine learning model. The surgical instrument prediction model 704 can be substantially similar in architecture to the second machine learning model 400, which is used for anatomical structure prediction. Further yet, the input window is analyzed by the depth estimation model 625 to generate the depth map 605. The machine learning models are trained using training data, which is substantially similar in structure to the surgical data 300. It should be noted that although separate machine learning models are described herein for detecting separate features of the surgical data, it should be understood that in some aspects, a single machine learning model, or a different combination of machine learning models (e.g., two models, three models) can be used to detect the features. The surgical training data can be recorded surgical data from prior surgical procedures or simulated surgical data, as described herein. The training data is pre-processed, for example, manually, to know the ground truth, and adjust the hyperparameters, and other parameters associated with the machine learning models during the training phase. The machine learning models are deemed to be trained once the output predictions from the models are within a predetermined error threshold of the ground truth and the corresponding confidence scores of the predictions are above a predetermined threshold.

During an inference phase, the trained machine learning models are input live surgical data 300, that has not been pre-processed. The machine teaming models, in the inference phase, generate the predictions. One or more machine learning models also output corresponding confidence scores associated with the predictions.

The outputs from each of the machine learning models are used by the output generator 160 to provide augmented visualization via the augmented reality devices 180. The augmented visualization can include the graphical overlays 502 being overlaid on the corresponding features (anatomical structure, surgical instrument, etc.) in the image(s) 302.

The output generator 160 can also provide a user feedback via the alert output system 170 in some aspects. The user feedback can include highlighting using graphical overlays 502 one or more portions of the image(s) 302 to depict proximity between the surgical instrument(s) and anatomical structure(s). Alternatively, or in addition, the user feedback can be displayed in any other manner, such as a message, an icon, etc., being overlaid on the image(s) 302.

In some aspects, to facilitate a real-time performance, the input window 320 is analyzed at a predetermined frequency, such as 5 times per second, 3 times per second, 10 times per second, etc. The analysis results in identification of locations of anatomical structures and surgical instruments in the images 302 that are in the input window 320. It can be appreciated that the video of the surgical procedure includes images 302 that are between two successive input windows 320. For example, if the video is captured at 60 frames per second, and if the input window 320 includes 5 frames, and if the input window 320 is analyzed 5 times per second, then a total of 25 frames from the captured 60 are analyzed. The remaining 35 frames are in between two successive input windows 320. It is understood that the capture speed, input window frequency, and other parameters can vary from one aspect to another, and that above numbers are examples.

For the frames, i.e., images 302, between two successive input windows 320, the locations of the anatomical structures and surgical instruments are predicted based on the locations predicted in the most recent input window 320. For example, a movement vector of the surgical instrument can be computed based on the changes in the location of the surgical instrument in the frames in the prior input window 320. The movement vector can be computed using a machine learning model, such as a deep neural network. The movement vector is used to predict the location of the surgical instrument in the subsequent frames after the input window 320, until a next input window 320 is analyzed.

The location of the anatomical structure(s) predicted by the machine learning model is also predicted in the frames between two successive input windows 320 in the same manner. The graphical overlays 502 that are used to overlay the images 302 to represent the predicted features (surgical instruments, anatomical structures, etc.) are accordingly adjusted, if required, based on the predicted locations. Accordingly, a smooth visualization, in real time, is provided to the user with lesser computing resources being used. In some aspects, the graphical overlays 502 can be configured to be switched off by the user, for example, the surgeon, and the system works without overlays 502, rather only generating the overlays 502 and/or other types of user feedback when an alert is to be provided (e.g., instrument within predetermined vicinity of an anatomical structure).

Figure 8:
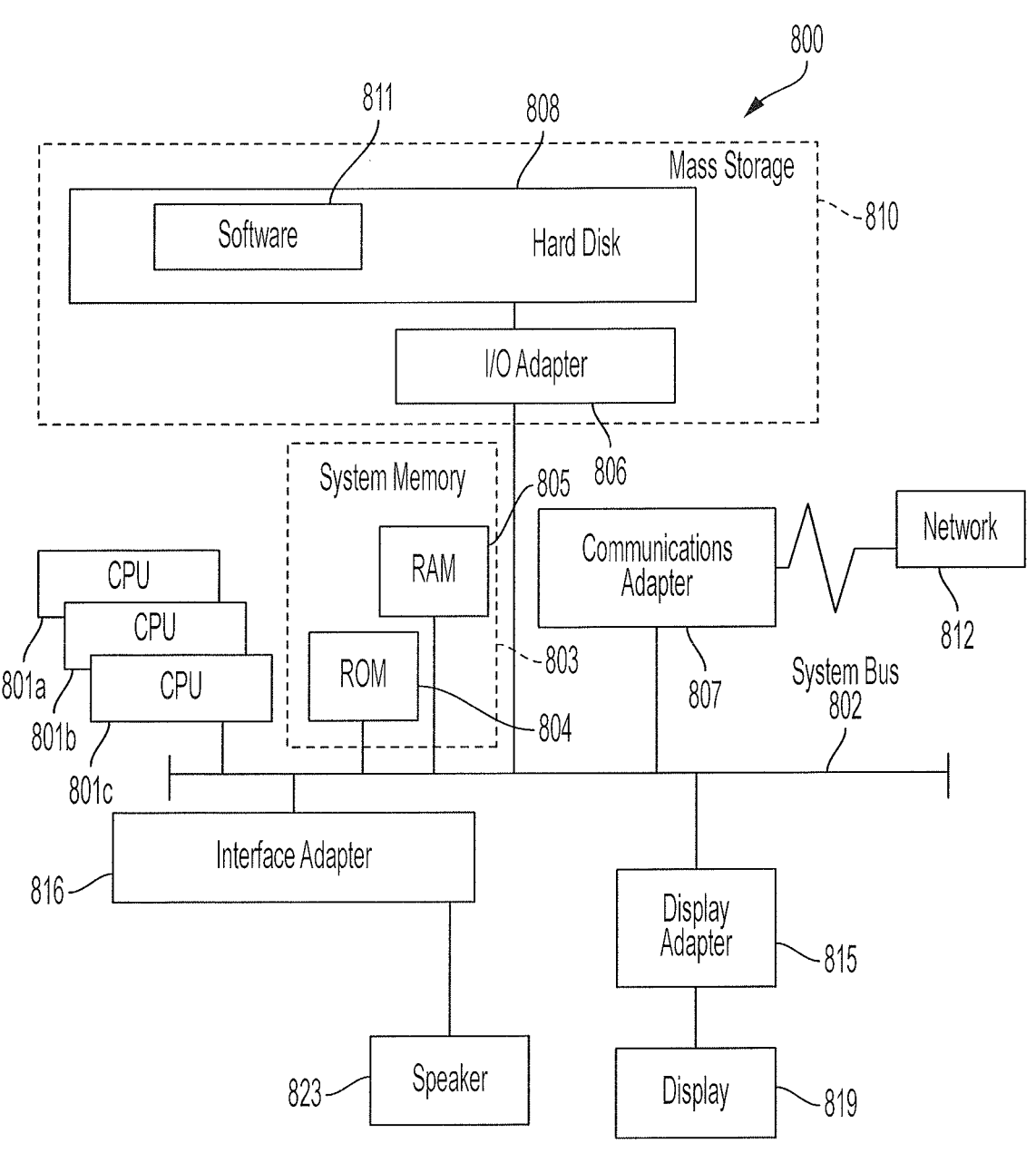
FIG. 8 depicts a computer system in accordance with one or more aspects.

Turning now to FIG. 8, a computer system 800 is generally shown in accordance with an aspect. The computer system 800 can be an electronic, computer framework comprising and/or employing any number and combination of computing devices and networks utilizing various communication technologies, as described herein. The computer system 800 can be easily scalable, extensible, and modular, with the ability to change to different services or reconfigure some features independently of others. The computer system 800 may be, for example, a server, desktop computer, laptop computer, tablet computer, or smartphone. In some examples, computer system 800 may be a cloud computing node. Computer system 800 may be described in the general context of computer system executable instructions, such as program modules, being executed by a computer system. Generally, program modules may include routines, programs, objects, components, logic, data structures, and so on that perform particular tasks or implement particular abstract data types. Computer system 800 may be practiced in distributed cloud computing environments where tasks are performed by remote processing devices that are linked through a communications network. In a distributed cloud computing environment, program modules may be located in both local and remote computer system storage media, including memory storage devices.

As shown in FIG. 8, the computer system 800 has one or more central processing units (CPU(s)) 801*a*, 801*b*, 801*c*, etc. (collectively or generically referred to as processor(s) 801). The processors 801 can be a single-core processor, multi-core processor, computing cluster, or any number of other configurations. The processors 801, also referred to as processing circuits, are coupled via a system bus 802 to a system memory 803 and various other components. The system memory 803 can include one or more memory devices, such as a read-only memory (ROM) 804 and a random access memory (RAM) 805. The ROM 804 is coupled to the system bus 802 and may include a basic input/output system (BIOS), which controls certain basic functions of the computer system 800. The RAM is read-write memory coupled to the system bus 802 for use by the processors 801. The system memory 803 provides temporary memory space for operations of said instructions during operation. The system memory 803 can include random access memory (RAM), read-only memory, flash memory, or any other suitable memory systems.

The computer system 800 comprises an input/output (I/O) adapter 806 and a communications adapter 807 coupled to the system bus 802. The I/O adapter 806 may be a small computer system interface (SCSI) adapter that communicates with a hard disk 808 and/or any other similar component. The I/O adapter 806 and the hard disk 808 are collectively referred to herein as a mass storage 810.

Software 811 for execution on the computer system 800 may be stored in the mass storage 810. The mass storage 810 is an example of a tangible storage medium readable by the processors 801, where the software 811 is stored as instructions for execution by the processors 801 to cause the computer system 800 to operate, such as is described hereinbelow with respect to the various Figures. Examples of computer program product and the execution of such instruction is discussed herein in more detail. The communications adapter 807 interconnects the system bus 802 with a network 812, which may be an outside network, enabling the computer system 800 to communicate with other such systems. In one aspect, a portion of the system memory 803 and the mass storage 810 collectively store an operating system, which may be any appropriate operating system to coordinate the functions of the various components shown in FIG. 8.

Additional input/output devices are shown as connected to the system bus 802 via a display adapter 815 and an interface adapter 816 and. In one aspect, the adapters 806, 807, 815, and 816 may be connected to one or more I/O buses that are connected to the system bus 802 via an intermediate bus bridge (not shown). A display 819 (e.g., a screen or a display monitor) is connected to the system bus 802 by a display adapter 815, which may include a graphics controller to improve the performance of graphics-intensive applications and a video controller. A keyboard, a mouse, a touchscreen, one or more buttons, a speaker, etc., can be interconnected to the system bus 802 via the interface adapter 816, which may include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI). Thus, as configured in FIG. 8, the computer system 800 includes processing capability in the form of the processors 801, and, storage capability including the system memory 803 and the mass storage 810, input means such as the buttons, touchscreen, and output capability including the speaker 823 and the display 819.

In some aspects, the communications adapter 807 can transmit data using any suitable interface or protocol, such as the internet small computer system interface, among others. The network 812 may be a cellular network, a radio network, a wide area network (WAN), a local area network (LAN), or the Internet, among others. An external computing device may connect to the computer system 800 through the network 812. In some examples, an external computing device may be an external web server or a cloud computing node.

It is to be understood that the block diagram of FIG. 8 is not intended to indicate that the computer system 800 is to include all of the components shown in FIG. 8. Rather, the computer system 800 can include any appropriate fewer or additional components not illustrated in FIG. 8 (e.g., additional memory components, embedded controllers, modules, additional network interfaces, etc.). Further, the aspects described herein with respect to computer system 800 may be implemented with any appropriate logic, wherein the logic, as referred to herein, can include any suitable hardware (e.g., a processor, an embedded controller, or an application-specific integrated circuit, among others), software (e.g., an application, among others), firmware, or any suitable combination of hardware, software, and firmware, in various aspects.

Figure 9:
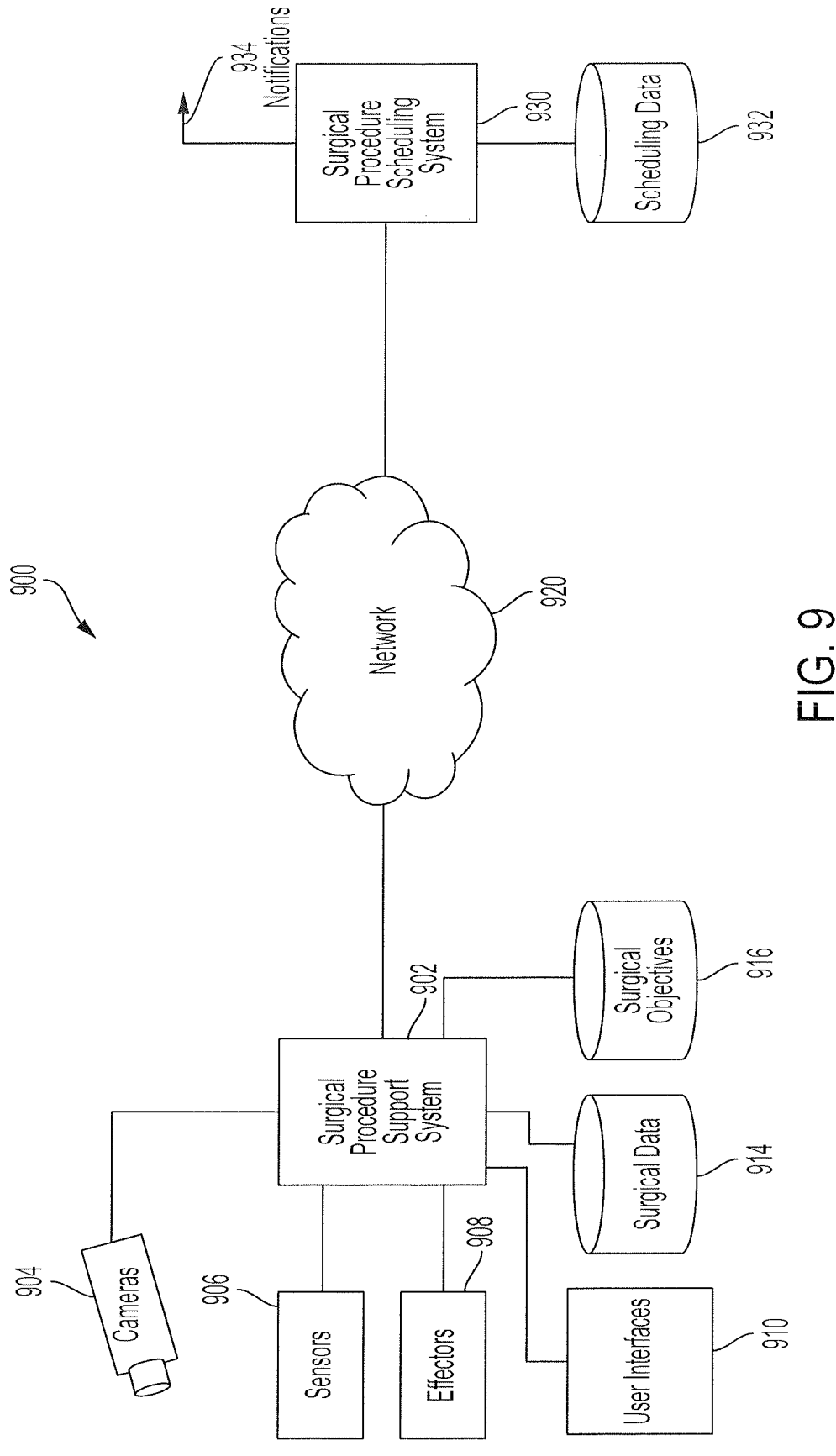
FIG. 9 depicts a surgical procedure system in accordance with one or more aspects

FIG. 9 depicts a surgical procedure system 900 in accordance with one or more aspects. The example of FIG. 9 depicts a surgical procedure support system 902 configured to communicate with a surgical procedure scheduling system 930 through a network 920. The surgical procedure support system 902 can include or may be coupled to the system 100. The surgical procedure support system 902 can acquire image data, such as images 302, using one or more cameras 904. The surgical procedure support system 902 can also interface with a plurality of sensors 906 and effectors 908. The sensors 906 may be associated with surgical support equipment and/or patient monitoring. The effectors 908 can be robotic components or other equipment controllable through the surgical procedure support system 902. The surgical procedure support system 902 can also interact with one or more user interfaces 910, such as various input and/or output devices. The surgical procedure support system 902 can store, access, and/or update surgical data 914 associated with a training dataset and/or live data as a surgical procedure is being performed. The surgical procedure support system 902 can store, access, and/or update surgical objectives 916 to assist in training and guidance for one or more surgical procedures.

The surgical procedure scheduling system 930 can access and/or modify scheduling data 932 used to track planned surgical procedures. The scheduling data 932 can be used to schedule physical resources and/or human resources to perform planned surgical procedures. Based on the surgical maneuver as predicted by the one or more machine learning models and a current operational time, the surgical procedure support system 902 can estimate an expected time for the end of the surgical procedure. This can be based on previously observed similarly complex cases with records in the surgical data 914. A change in a predicted end of the surgical procedure can be used to inform the surgical procedure scheduling system 930 to prepare the next patient, which may be identified in a record of the scheduling data 932. The surgical procedure support system 902 can send an alert to the surgical procedure scheduling system 930 that triggers a scheduling update associated with a later surgical procedure. The change in schedule can be captured in the scheduling data 932. Predicting an end time of the surgical procedure can increase efficiency in operating rooms that run parallel sessions, as resources can be distributed between the operating rooms. Requests to be in an operating room can be transmitted as one or more notifications 934 based on the scheduling data 932 and the predicted surgical maneuver.

As surgical maneuvers and steps are completed, progress can be tracked in the surgical data 914, and status can be displayed through the user interfaces 910. Status information may also be reported to other systems through the notifications 934 as surgical maneuvers are completed or if any issues are observed, such as complications.

The reports/views/annotations and other information described herein is added to an electronic medical record (EMR) in one or more cases. In some aspects, the information about specific surgical procedures can be stored in the patient record associated with the patient that was operated upon during the surgical procedure. Alternatively, or in addition, the information is stored in a separate database for later retrieval. The retrieval can be associated with the patient's unique identification, such as EMR-identification, social security number, or any other unique identifier. The stored data can be used to generate patient-specific reports. In some aspects, information can also be retrieved from the EMR to enhance one or more operations described herein. In one or more aspects, an operational note may be generated, which includes one or more outputs from the machine learning models. The operational note may be stored as part of the EMR.

Laparoscopic cholecystectomy is a common surgery in which the gallbladder is removed. This involves exposing the critical structures (cystic duct and artery), clipping and dividing them, then extracting the gallbladder (see 503 in FIG. 5). Complications can occur when the structures are misidentified or confused with the common bile duct, particularly as they may be difficult to distinguish without thorough dissection. Official guidance has encouraged that surgeons establish "critical view of safety" (CVS) before clipping and division. In CVS, both structures can clearly and separately be identified, and traced as they enter the gallbladder.

Aspects of the technical solutions described herein provide computer assistance in achieving CVS to improve surgical safety and workflow by providing improvements in computer vision and machine learning. Existing systems have demonstrated a proof of principle approach using binary CVS classification. Some existing techniques create a bounding box detection system, based on anatomical landmarks that included the common bile duct and cystic duct but not the cystic artery. Some existing techniques have used joint segmentation of the hepatobiliary anatomy and classification of CVS.

Technical solutions described herein instead directly detect structures that are the critical structures that surgeons must identify and divide. Aspects of the technical solutions herein accordingly facilitate guiding surgical workflow because once CVS has been achieved, then by definition the structures are already identified and dissected. Aspects of the technical solutions described herein facilitate detecting the critical structures. Aspects of the technical solutions described herein outperform conventional segmentation by using label relaxation to address technical challenges where the ground truth labels are ambiguous about where the structures are in the input images/video.

Figure 10:
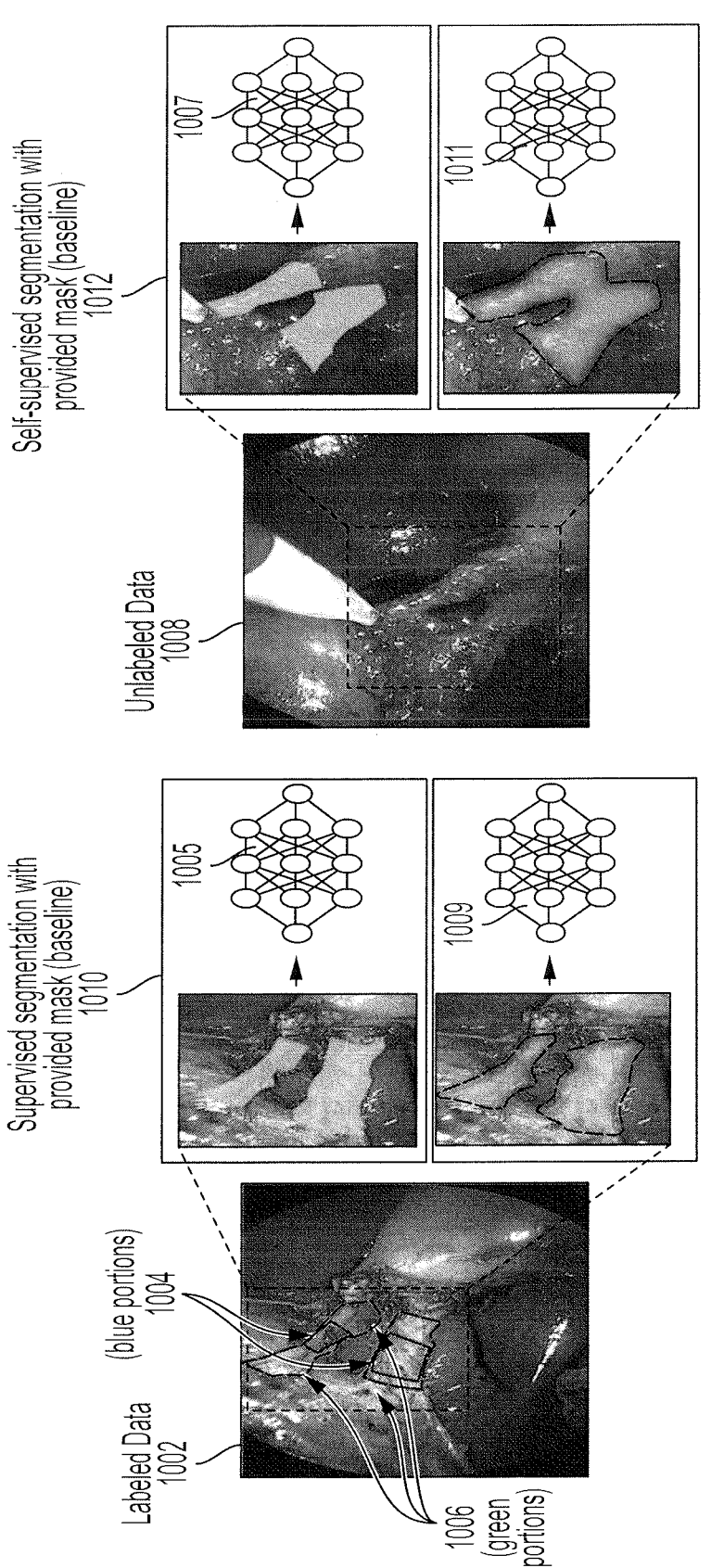
FIG. 10 depicts improvements to machine learning provided by one or more aspects of the technical solutions herein using label relaxation.

FIG. 10 depicts improvements to machine learning provided by one or more aspects of the technical solutions herein using label relaxation. The machine learning models are trained using labeled ground truth data. Hence, accuracy of the labeled ground truth data is important. Accuracy of the machine learning model's predictions depends on the accuracy of the labeled ground truth data used during training. As can be seen in FIG. 10, there can be scenarios where the labeled data 1002 can have some ambiguity. The ambiguity can be because of difficulty in labeling structures separately, for example, due to overlap in structures. While several different examples exist, the view in the labeled data 1002 depicts a view of a cystic artery and cystic duct, in which labels 1004, 1006 are both valid, and as can be seen are inseparable. Such ambiguous labeling is a technical challenge for training the machine learning models using supervised segmentation with provided mass (1010). Conventional segmentation approaches struggle to perform well in this task because of the ambiguous and subjective nature of the annotations. This problem is exacerbated by the use of conventional one-hot encoding: a given pixel is assigned as either 100% structure or 100% background class. This impairs generalization and can cause the machine learning model(s) to have false negatives.

Some aspects of the technical solutions herein incorporate pseudo-label self-supervision (1012), using unlabeled data (1008) to address such technical challenges with ambiguous labels. The labeled data (1002) and unlabeled data (1008) can be obtained from multiple videos of prior surgical procedures for self-supervision. In comparison to supervised segmentation using ambiguous labels (1010), the self-supervised segmentation using unlabeled data (1012) improve clinical significance when detecting critical structures.

In some aspects of the technical solutions herein the labeled data 1002, even with ambiguous labels, is used to train the machine learning models using label relaxation. Here, the critical structures are labeled and treated as a single foreground class, with the rest of the image considered as background. This poses the technical problem as a binary segmentation problem. To address this technical challenge, in some aspects of the technical solutions herein, rather than using segmentation, the machine learning models are trained for heatmap regression, where the ground truth heatmap is derived from the original annotations' Euclidean distance transforms.

Given a binary, segmentation ground truth $x_k$ for structure k, aspects of the technical solutions described herein define the relaxed label as $$x'_k = 1 - \exp\frac{-edt(x_k \oplus t)}{d}$$

where edt(•) is the Euclidean distance, $\oplus$t represents dilation with a square of t pixels, and d is a parameter to control the relaxation. Each $x_i$ is then normalized by its maximum value to allow use as a probability heatmap. Where heatmaps overlap for different structures within an image, the maximum value is used.

Through such a heatmap regression method, central pixels are assigned high confidence, and more distant pixels are assigned low confidence as shown in FIG. 10. This systematic label relaxation reflects the ambiguity of the structure boundaries, and copes better with variation in annotations (e.g., 1009, 1011).

Labelling medical imagery is widely recognized as a bottleneck due to its difficulty, high time cost and compliance challenges. This is particularly true for surgical video, which generates large amounts of unstructured data. Aspects of the technical solutions described herein further improve performance of a machine learning model by using unlabeled data via self-supervision in addition to the heatmap regression. Unlike existing techniques that use self-supervision in endoscopic surgery, which uses generative models and consistency-based losses, aspects of technical solutions described herein use a pseudo-label approach that requires minimal computational overhead.

After training the machine learning models 1005 on labeled data 1002, the predictions from the machine learning models 1005 are used to provide pseudo-labels in unlabeled data 1004. This serves as a teacher in a teacher-student machine learning architecture, where a newly initialized student is trained on both datasets. Combined with regularization, the student learns a superior distillation of feature space compared to its teacher.

In some aspects of the technical solutions described herein the machine learning models 1009, 1011 are convolutional neural networks, with FCN segmentation architecture for the machine learning models 1005, 1007 used for segmentation. The artificial neural networks in one or more aspects use ResNet101, although, other types of network architectures can be used. For the segmentation and self-supervised segmentation models 1005, 1007 the FCN is trained with cross-entropy loss. FCN can use class frequency weighted cross-entropy loss, equally weighted cross-entropy loss, or other techniques. To assist with comparison, the heatmap machine learning model 1009 is kept similar to the segmentation model 1005, by using SoftMax to convert raw logits to a heatmap. The heatmap machine learning model 1009 uses soft cross-entropy loss with relaxed ground truth label as described herein.

The machine learning models 1005, 1007, 1009, 1011 are trained until convergence. During training, the machine learning models 1005, 1007, 1009, 1011 use random image augmentations (padding, cropping, flipping, blurring, rotation, noising) and model regularization via dropout. Hyperparameter tuning for augmentation, and/or label relaxation parameters t and d can be performed in one or more aspects. Alternatively, predetermined values can be used for t and d.

The machine learning models 1005, 1009 are trained in one or more aspects as a baseline segmentation model, a baseline heatmap model. Predictions from the machine learning models 1005, 1009 are used to train the variants of both models, i.e., the machine learning models 1007, 1011 using self-supervision to exploit the unlabeled data 1004.

Table 1 shows pixel-level metrics ordered by method (segmentation versus heatmap method described herein) and whether self-supervision was used. As can be seen, the heatmap detection described herein consistently performs better than segmentation in intersection-over-union (IoU) regardless of whether self-supervision is used. IoU is an evaluation metric used to measure the accuracy of an object detector on a particular dataset. The self-supervision approach improves performance further. Self-supervision improves accuracy in general, but is particularly beneficial for a few difficult cases. The example of table 1 generally illustrates advantages of heatmap models that can be realized over segmentation. It is noted that other values, including higher accuracy results may be achieved using aspects disclosed herein, and thus, table 1 should not be construed as limiting the scope of the disclosure.

TABLE 1

| Method | SS | Val | | | Test | | |
|---|---|---|---|---|---|---|---|
| | | IoU | Precision | Recall | IoU | Precision | Recall |
| Segmentation | x | .547 | .764 | .658 | .501 | .869 | .542 |
| Segmentation | ✓ | .562 | .807 | .649 | .512 | .849 | .563 |
| Heatmap | x | .644 | .836 | .750 | .618 | .811 | .721 |
| Heatmap | ✓ | .681 | .867 | .761 | .649 | .823 | .755 |

Figure 11:
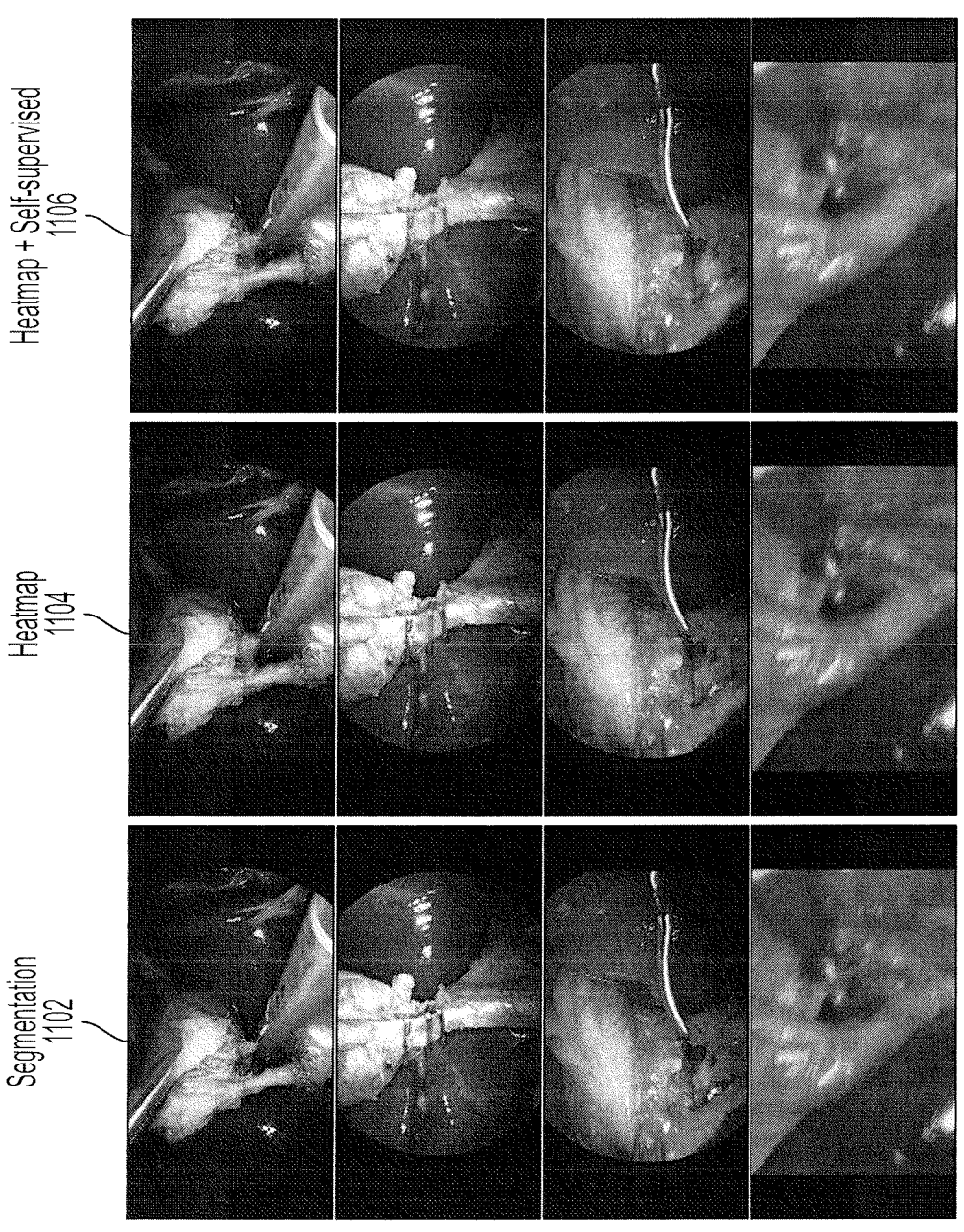
FIG. 11 depicts comparison of results in an example scenario obtained by using the different types of machine learning models according to one or more aspects.

FIG. 11 depicts comparison of results in an example scenario obtained by using the different types of machine learning models according to one or more aspects. Structure detection results 1102 are from segmentation machine learning model 1005, structure detection results 1104 are from heatmap machine learning model 1009, and structure detection results 1106 are from heatmap self-supervised machine learning model 1011.

Each row depicts the same image processed by each of the machine learning models. In rows 1, 3 and 4, self-supervision slightly improved the accuracy, but the overall detection was not changed significantly, and hence the IoU remains similar. In row 2, however, the accuracy improvement was much larger as the supervised model entirely misses the cystic artery, whereas the self-supervised model detected it. Table 2 shows metrics for frame-level presence detection, where artery and duct detections must exceed an IoU threshold to count as true positives in a given frame. In other words, IoU detection score below a predetermined threshold is counted as a false positive. Such statistics are conservative, as a lower IoU overlap may nonetheless be fairly accurate given the ambiguity of ground truth annotation extent. Nevertheless, results show a similar pattern to the pixel-level performance metrics, with the heatmap method outperforming segmentation, and self-supervision improving the models' performance. Notably, the increased pixel-level precision of segmentation methods does not translate to structure detection, where the heatmap method performs better by every metric. In the specific example of Table 2, higher-level presence detection metrics, evaluated with IoU threshold 0.5 to count as a true positive detection. It is understood that a different IoU score can be used as the predetermined threshold in other aspects. The example of table 2 generally illustrates advantages of heatmap models that can be realized over segmentation. It is noted that other values, including higher accuracy results may be achieved using aspects disclosed herein, and thus, table 2 should not be construed as limiting the scope of the disclosure.

TABLE 2

| Method | SS | Val | | | Test | | |
|---|---|---|---|---|---|---|---|
| | | F1 | Precision | Recall | F1 | Precision | Recall |
| Segmentation | x | .597 | .599 | .594 | .615 | .626 | .606 |
| Segmentation | ✓ | .640 | .640 | .641 | .616 | .616 | .617 |
| Heatmap | x | .716 | .721 | .711 | .694 | .703 | .685 |
| Heatmap | ✓ | .811 | .833 | .790 | .749 | .750 | .749 |

Figure 12:
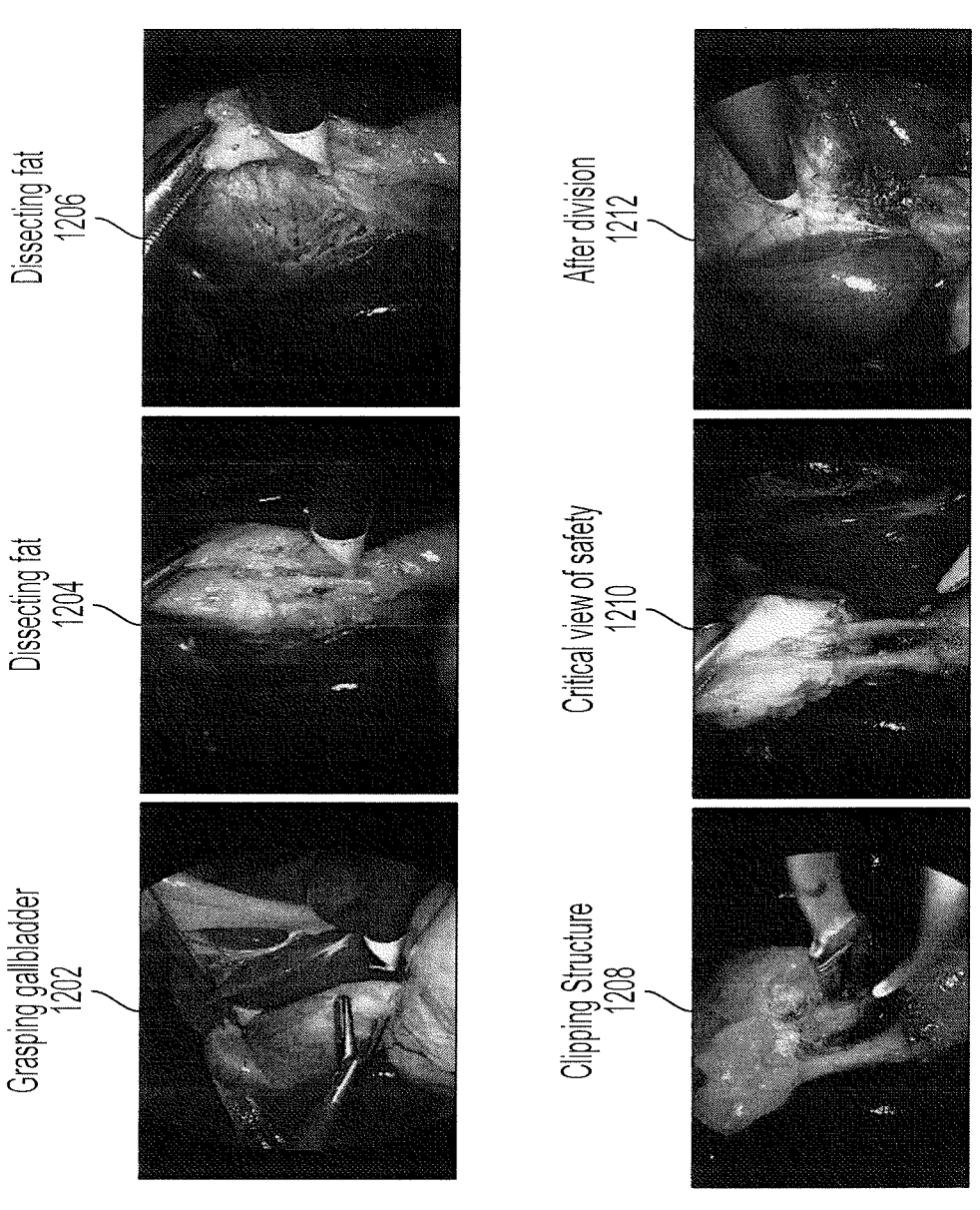
FIG. 12 shows example frames and model outputs from an excerpt of a laparoscopic cholecystectomy video.

FIG. 12 shows example frames and model outputs from an excerpt of a laparoscopic cholecystectomy video. Aspects of the technical solutions described herein do not suffer false detections before structures are visible (1202), although similar shapes near a tool tip can be ambiguous, particularly if such shapes are visible near the gallbladder. Even when the structures are heavily coated by fat, aspects of the technical solutions described herein tend to recognize them at least partially (1204, 1206). The structure being clipped in the image does not prevent detection (1208). Structures remain detectable after division (1212). In some aspects, using surgical phase recognition is used to deactivate detection after division of structures. Critical view of safety (1210) is facilitated by the aspects described herein.

The heatmap based machine learning models described herein are more accurate than segmentation based machine learning models, as shown in low-level pixel metrics such as IoU and higher-level presence detection such as F1 score.

Accordingly, aspects of the technical solutions described herein detect the critical structures during surgical procedures, such as laparoscopic cholecystectomy. When trying to detect structures with ambiguous extent and challenging annotations, a heatmap-based approach based on label relaxation is used to improve performance over baseline techniques, such as segmentation based machine learning models. Self-supervision provided further improvement by using unlabeled data for additional training. Automatic detection of critical structures in surgery improves computing systems used to store and automatically process surgical data. Further, aspects of the technical solutions described herein improve surgical safety, training and workflow and ultimately patient outcomes.

It should be noted that although aspects herein are described using laparoscopic cholecystectomy as an example, the technical solutions provided herein can be used for any other type of surgical procedures and are not limited to a particular type of surgical procedure.

As noted herein, detection of surgical instruments in minimally invasive surgery video frames allows automatic generation of offline surgical analytics, that can provide valuable information for improving surgical procedures. Additionally, surgical instrument detection can provide real-time decision support during the surgery and notification of preventable risks during computer assisted interventions. Accurate models are required to successfully use decision support systems during surgical procedures. Current machine learning approaches typically estimate the location and type of surgical instruments via either bounding box detection or semantic segmentation. Surgical instruments (or tool) detection models generally rely on annotated bounding boxes during training. This has a major limitation for instrument detection as the annotated bounding boxes include a high number of background pixels due to the elongated dimensions of the surgical instruments, which might impede a model from learning discriminative features of the instruments. Alternatively, segmentation models directly estimate the probability of each pixel to belong to a specific instrument type by relying on fine-grained pixel-wise segmentation mask annotations. While masks solve the aforementioned technical challenge faced by bounding boxes, the annotation cost significantly grows up to almost two orders of magnitude for annotating masks with respect to only annotating frame-level labels or bounding boxes. In practice, the annotation of datasets with masks at scale can be unfeasible, which can prevent models from achieving the generalization and robustness required to be applied in real-world applications.

To address the technical challenges above and leverage the strengths of both workstreams, aspects of technical solutions described herein use a multi-task machine learning model ("model") that jointly learns to estimate bounding boxes and masks for surgical instruments. The model aggregates information from the multiple tasks by using a shared backbone as an encoder, while having a head for each individual task: instrument classification, bounding box regression and segmentation. While the classification and regression heads allow the model to localize and classify surgical instruments using scalable annotations, the segmentation head achieves the detailed pixel-wise annotations. To alleviate the burden of expensive pixel-wise annotation on large datasets, one or more aspects of technical solutions described herein use a training framework that accounts for missing masks and uses weakly-supervised loss computed on frame-level labels, which can be freely obtained from the bounding box annotations. Experimental comparison shows that the model achieves detection and segmentation performance on par with fully-supervised alternatives, while requiring as little as 1% of the masks in training.

Existing solutions to detect and localize surgical tools in video include semantic segmentation and tool detection. Segmentation models are able to segment instruments against background (binary segmentation), tool types (semantic segmentation) or tools instances (instance segmentation). Some existing solutions segment entire instruments instances instead of pixel-wise segmentation.

As a further example, existing machine learning models for detecting surgical instruments can be anchor-based and based on a convolutional backbone with a ResNet architecture, that generates feature maps at different scales, and two task-specific heads that perform object classification and bounding box regression from the feature pyramid. This approach faces a foreground-background class imbalance during training. This is handled by using the focal loss, a variation of the cross-entropy loss function that down-weights the loss assigned to well-classified examples. Some existing solutions jointly scale up model width, depth, and resolution to meet real-time requirement without sacrificing detection accuracy. One example of a model computes a feature pyramid using EfficientNet. Some existing solutions use a weighted bi-directional feature pyramid network (BiFPN) to leverage the multi-scale feature information. Further, some existing solutions use joint detection and segmentation. For example, some existing solutions use a model for semi-supervised object segmentation that relies on single manual bounding box initialization to produce class-agnostic object masks and rotated bounding boxes with a fully-convolutional siamese model. Using weak supervision, a multi-task model to perform detection and segmentation with a weakly-supervised cyclic policy can be used to complement the learning of both tasks simultaneously in such existing solutions. Further, the existing solutions use weakly-supervised convolutional model to estimate the presence and localization of surgical instruments using only frame-label annotations. However, the performance of these weakly-supervised models is still far from fully supervised ones.

Aspects of the technical solutions described herein address such technical challenges with machine learning models that are used for detecting the surgical tools and instruments by facilitating detection and segmentation jointly. Consider $x \in \{0, 255\}^{W,H,C}$ is an RGB image with width W, height H and C=3 color channels. Let $D(\cdot)$: $x \rightarrow (B^{N,4}, C^N, M^{W,H,M})$ be a joint detection and segmentation model that localizes and classifies surgical instruments within x which outputs are a set of bounding boxes ($B^{N,4}$), their corresponding estimated classes ($C^N$), and a segmentation mask ($M^{W,H,M}$), with N being the number of detected instruments and M the number of considered instrument types.

Figure 13:
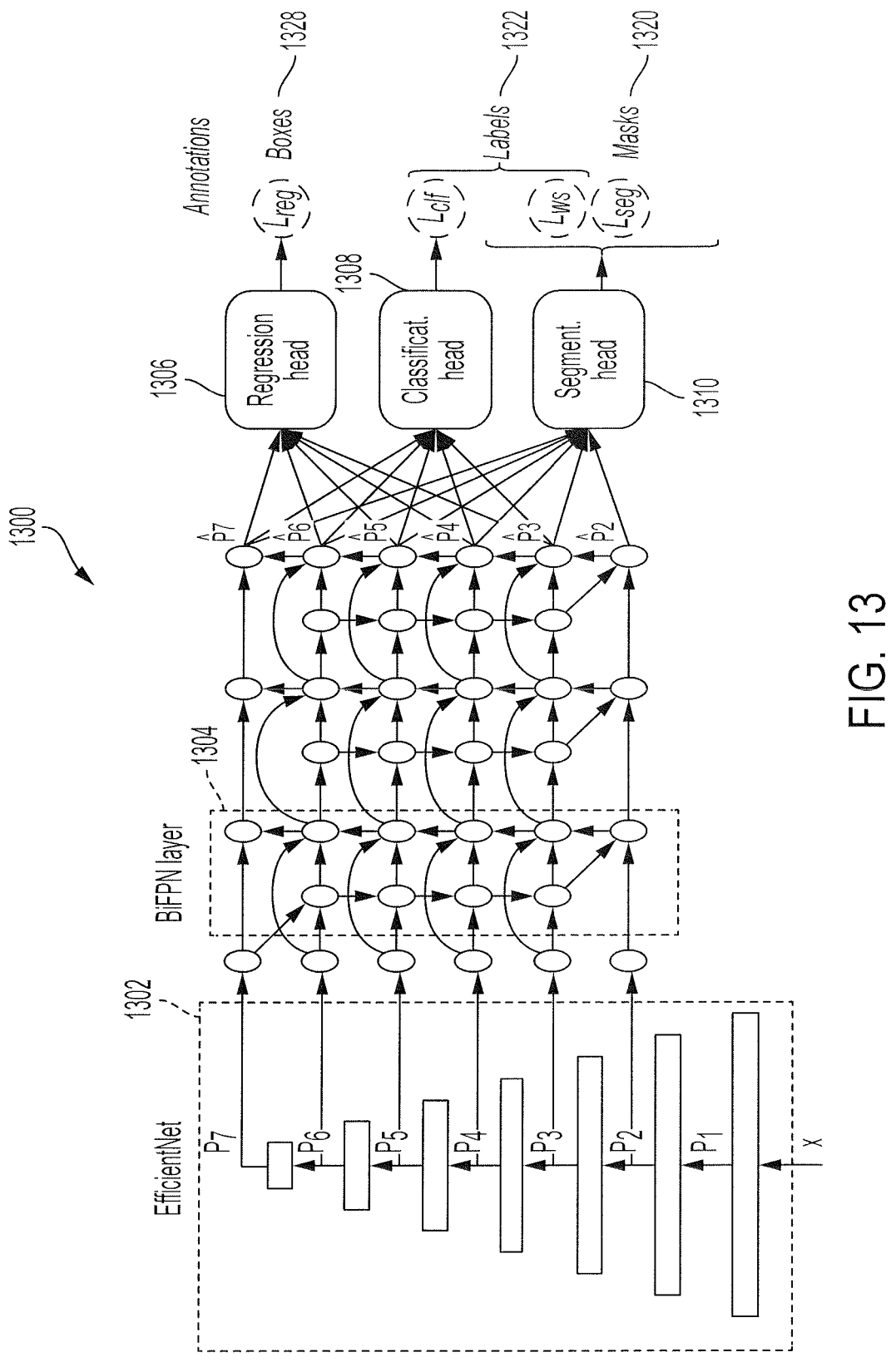
FIG. 13 depicts a block diagram of an architecture of a multi-task machine learning model for joint detection and segmentation of surgical instruments according to one or more aspects.

The technical problem of the joint detection and segmentation is formulated as a multi-task learning problem. FIG. 13 depicts a block diagram of an architecture of a multi-task machine learning model for joint detection and segmentation of surgical instruments according to one or more aspects. The architecture 1300 includes an encoder 1302, multi-scale feature fusion 1304, and multiple task heads 1306, 1308, 1310. As one example, the encoder 1302 can be an EfficientNet backbone, and the multi-scale feature fusion 1304 can be a set of bi-directional feature pyramid networks (BiFPNs). It will be understood that other types of encoders and feature fusion can be used with corresponding task heads 1306-1310, where task heads 1306-1310 can include any number of task heads to process outputs of the multi-scale feature fusion 1304. For purposes of explanation, in the example of FIG. 13, the task heads 1306, 1308, 1310 are for the tasks of bounding box regression, bounding box classification, and segmentation, respectively. The encoder 1302 can be a share backbone that acts as a joint representation learning module with an aim to learn multi-level feature representations suitable for all the tasks, task head 1306 can provide bounding box regression, task head 1308 can provide bounding box classification, and task head 1310 can provide segmentation. Input x can include one or more frames and/or data inputs. Having x as input, the encoder 1302 $\beta(.)$: $x \rightarrow P$ can generate a pyramid of features at S scales $$P = (p_s)_{s=1}^{s=S}.$$

The feature pyramid can be fed to the next layers of the multi-scale feature fusion 1304. For example, when implemented as one or more bi-directional feature pyramid networks (BiFPNs), layers of the multi-scale feature fusion 1304 can fuse the features across scales while maintaining their number and resolution $\gamma(.)$: $\mathbb{P} \rightarrow \hat{\mathbb{P}}$. The three task heads 1306, 1308, 1310 guide the learning of the encoder 1302 and the multi-scale feature fusion 1304 to learn more discriminative and complementary features to further improve the tasks, while adapting generated features for task specific problems. The tasks can include, for instance, bounding box regression, bounding box classification, and segmentation.

In some aspects, as described herein, the amount of training data (annotated masks) used for the machine learning model 1300 is limited (because it is expensive to generate/annotate). Hence, the technical challenge of the lack of data is compensated by employing weak supervision is used to improve the performance of the machine learning model 1300.

Figure 14:
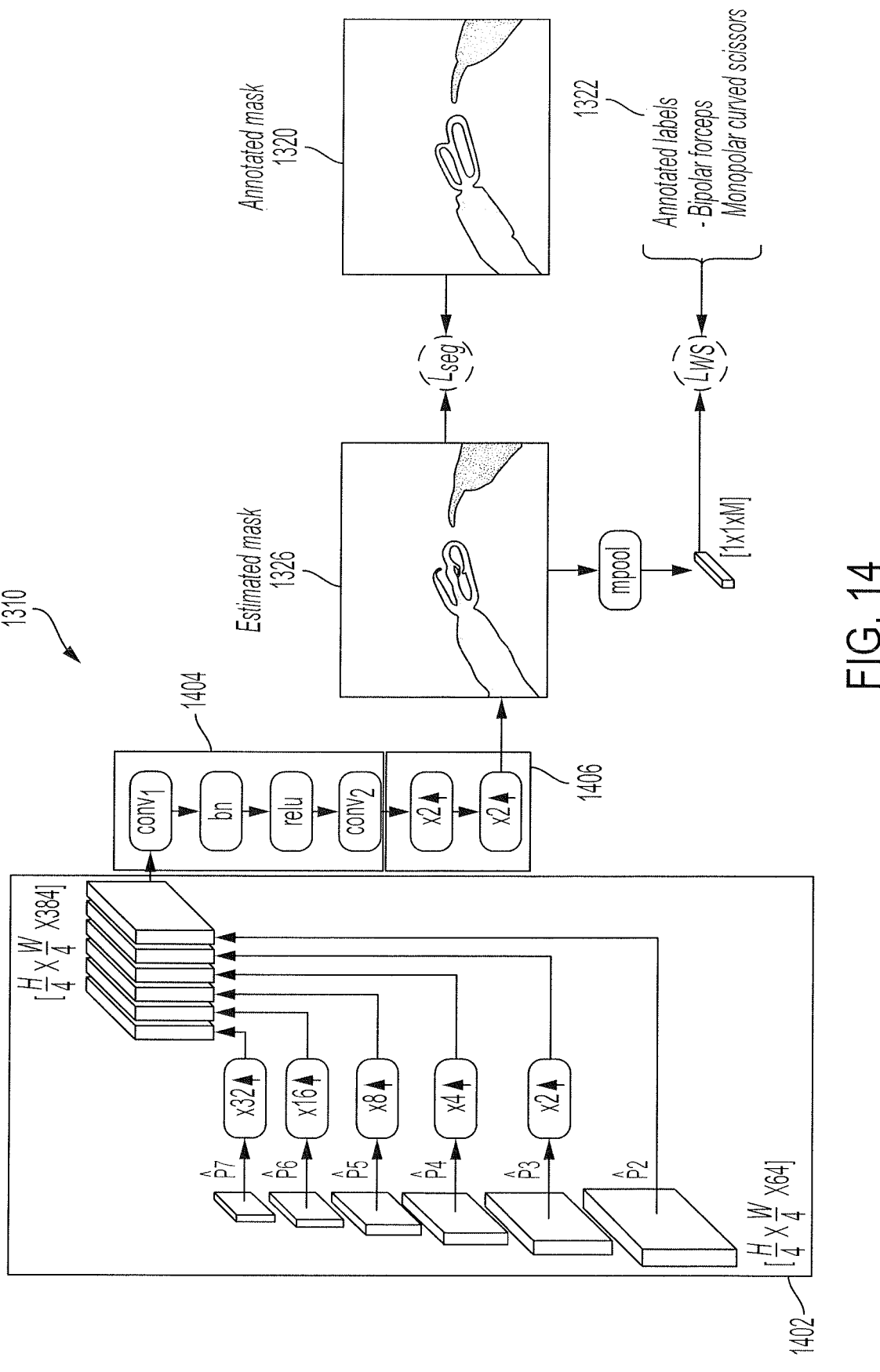
FIG. 14 depicts an architecture for segmentation according to one or more aspects.

The segmentation of task head 1310 aims to generate a mask 1320 MW,H,M from the fused feature pyramid $\hat{\mathbb{p}}$. FIG. 14 depicts an architecture for segmentation of task head 1310 according to one or more aspects. The segmentation of task head 1310 can include: feature up-sampling and concatenation (1402), convolutional block (1404), and up-sampling (1406).

At block 1402, to make use of the information contained in the multiple scales of the fused feature pyramid, $P^$, the S−2 feature maps with smallest spatial resolution $$(\hat{p}_s)_{s=1}^{s=S}$$

are first up-sampled to the spatial resolution of $\hat{p}_2$ using bi-linear interpolation. Then, the S−1 feature maps are concatenated.

$$\hat{\mathbb{P}} = (\hat{p}_2, U_2(\hat{p}_3), U_2(\hat{p}_4), U_2(\hat{p}_5), U_2(\hat{p}_6), U_2(\hat{p}_7)) \qquad (1)$$

where $U_2(\bullet)$ is the bilinear interpolation operation that up-samples the feature map to the resolution of $\hat{p}_2$, and $(\bullet, \ldots, \bullet)$ represents the concatenation operation.

At block 1404, a convolutional block is then applied to achieve a feature map with same number of channels as number of considered instrument types (i.e., M) as $$\tilde{M} = conv_2(relu(bn(conv_1(\hat{p})))) \tag{2}$$

where $conv_1(\bullet)$ is a 2D convolution with kernel ($1\times1$) and $S-1\times64$ channels that fuses the features with different resolutions, $bn(\bullet)$ is a batch normalization layer, $relu(\bullet)$ is the Rectified Linear Unit (ReLU) operation, and $conv_2(\bullet)$ is a 2D convolution with kernel ($1\times1$) and M channels to reduce the number of channels to the number of instrument types, M.

At block 1406, $\tilde{M}$ is up-sampled to generate masks 1320 with same dimensions as the input images $$M = U_0(\tilde{M}) \tag{3}$$

where $U_0(\bullet)$ is the bilinear interpolation operation that up-samples the feature map to the resolution of the input image x.

Some aspects of the technical solutions described herein use semi-supervised learning with weak supervision. When the annotated mask 1320, $\tilde{M}$, is available for a given sample, the cross-entropy loss function is used for training the segmentation at task head 1310. However, as not all samples have an annotated mask 1320, in each batch the cross-entropy loss is weighted by the ratio of samples with annotated masks A to the total number of samples within the batch B as $$L_{seg} = \frac{A}{B} L_{CE}(M, \tilde{M}) \tag{4}$$

where $L_{CE}(\bullet,\bullet)$ is the cross-entropy loss function. Thus, batches with fewer annotated samples have a lower weight.

In addition, when a mask is not available, aspects of the segmentation at task head 1310 are trained to compare condensed mask presence labels with only frame-label annotations 1322, where the estimated mask 1326 is condensed using global max pooling within a single value per instrument type as $$O = mpool(M) \tag{5}$$

where $mpool(\bullet)$ is the 2D maxpool operation with kernel size (H, W) that generates a vector $O \in R^{1,1,M}$. The information within $O$ resembles the presence/absence of each instrument type within the frame. These outputs indicate the presence of a given instrument type within the frame. Note that these annotations, which are the cheapest to generate, are already available to the model within the bounding box annotations 1328.

The weakly-supervised loss is the cross entropy between $O$ and the instrument type frame-level annotations, $\bar{O}$ as $$L_{ws} = L_{CE}(O, \bar{O}) \tag{6}$$

Lws($\bullet$) is computed for all frames, regardless of whether their mask is provided or not. Accordingly, the full loss used to train the encoder 1302, multi-scale feature fusion 1304, and task heads 1306-1310 can be defined as $$L = w_{reg} \cdot L_{reg} + w_{clf} L_{clf} + w_{seg} L_{seg} + w_{ws} L_{ws} \tag{7}$$

where ($L_{reg}$, $L_{clf}$) is the weighted focal loss, and $w_{reg}$, $w_{clf}$, $w_{seg}$, and $w_{ws}$ are weights of regression, classification, segmentation, and weak supervision losses that tune the contribution of each loss.

In one or more aspects, the machine learning model 1300 is implemented as a neural network. The architecture of the neural network can use, as a backbone, the EfficientNet-D0 neural network (e.g., for encoder 1302) with pre-trained weights on ImageNet. The BiFPN layer (e.g., of multi-scale feature fusion 1304) can be modified to aggregate S=6 feature scales instead of five for improved segmentation accuracy. The five smallest scales are used for the regression and classification for task heads 1306, 1308. Images can be downscaled to 512×512 pixels and data augmentation that includes geometrical and color transformations are used. A sampler to balance the number of different instruments present in each batch is used. The models can be trained for a predetermined number of epochs. The results obtained in the last epoch are reported. The proposed loss (Eq. 7) weights are empirically set. For example, wreg=1, wclf=5, wseg=700, and wws=5. It is understood that the values described above are examples, and can be set differently in other aspects.

Figure 15:
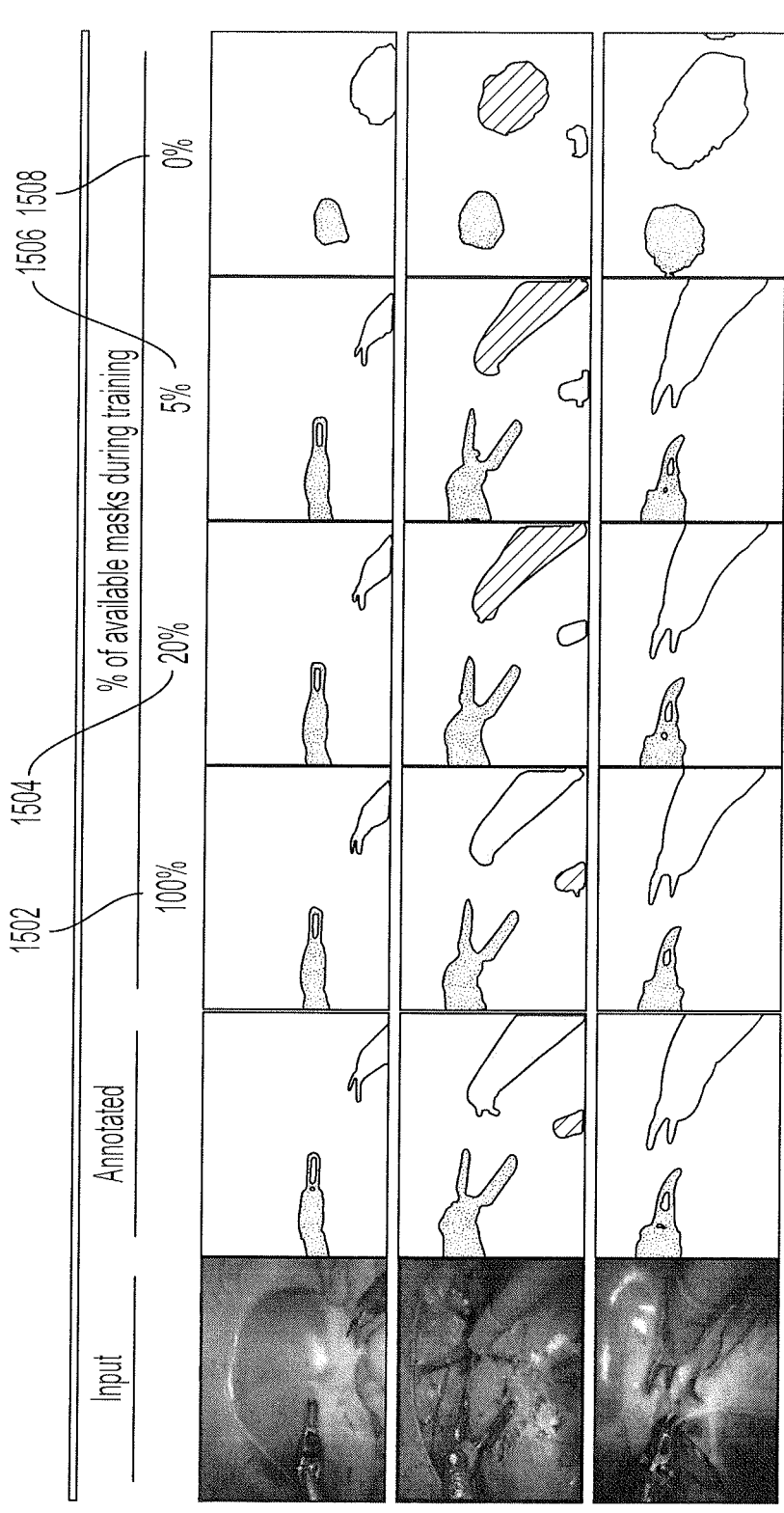
FIG. 15 depicts example results of using a machine learning model to perform joint detection and segmentation of surgical instruments according to one or more aspects.

When comparing against state-of-the-art joint detection and segmentation models, the machine learning model 1300 obtains improved results against the fully annotated alternatives while only requiring a 1% of masks to be annotated. Three visual segmentation samples, one per each sequence of the testing split, are displayed in FIG. 15 for models trained using 100% (1502), 20% (1504), 5% (1506), and 0% (1508) of annotated masks. The estimated masks maintain the quality even when the available masks are reduced to 5% (1506). Some classification errors are observed in the second sequence when limited masks are used.

Accordingly, aspects of the technical solutions described herein provide a multi-task machine learning model that jointly learns to detect and segment surgical instruments. A weakly-supervised adaptive loss is also used in some aspects, that enables the learning of segmentation masks when only a fraction of masks are available during training by supervising the learning with frame-level annotations. Results show that the model 1300 provided herein obtains improved results compared to a fully-supervised alternative, while only requiring a 1% of the masks.

It should be noted that although some of the drawings depict endoscopic videos being analyzed, the technical solutions described herein can be applied to analyze video and image data captured by cameras that are not endoscopic (i.e., cameras external to the patient's body) when performing open surgeries (i.e., not laparoscopic surgeries). For example, the video and image data can be captured by cameras that are mounted on one or more personnel in the operating room, e.g., surgeon. Alternatively, or in addition, the cameras can be mounted on surgical instruments, walls, or other locations in the operating room.

The present invention may be a system, a method, and/or a computer program product at any possible technical detail level of integration. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine-dependent instructions, microcode, firmware instructions, state-setting data, configuration data for integrated circuitry, or either source-code or object code written in any combination of one or more programming languages, including an object-oriented programming language such as Smalltalk, C++, or the like, and procedural programming languages, such as the "C" programming language or similar programming languages. The computer-readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some aspects, electronic circuitry including, for example, programmable logic circuitry, field-programmable gate arrays (FPGA), or programmable logic arrays (PLA) may execute the computer-readable program instruction by utilizing state information of the computer-readable program instructions to personalize the electronic circuitry, in order to perform aspects of the present invention.

Aspects of the present invention are described herein with reference to flowchart illustrations and/or block diagrams of methods, apparatus (systems), and computer program products according to aspects of the invention. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other devices to produce a computer-implemented process, such that the instructions which execute on the computer, other programmable apparatus, or other device implement the functions/acts specified in the flowchart and/or block diagram block or blocks.

The flowchart and block diagrams in any of the Figures illustrate the architecture, functionality, and operation of possible implementations of systems, methods, and computer program products according to various aspects of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various aspects of the present invention have been presented for purposes of illustration but are not intended to be exhaustive or limited to the aspects disclosed. Many modifications and variations will be apparent to those of ordinary skill in the art without departing from the scope and spirit of the described aspects. The terminology used herein was chosen to best explain the principles of the aspects, the practical application or technical improvement over technologies found in the marketplace, or to enable others of ordinary skill in the art to understand the aspects described herein.

Various aspects of the invention are described herein with reference to the related drawings. Alternative aspects of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains," or "containing," or any other variation thereof are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any aspect or design described herein as "exemplary" is not necessarily to be construed as preferred or advantageous over other aspects or designs. The terms "at least one" and "one or more" may be understood to include any integer number greater than or equal to one, i.e., one, two, three, four, etc. The terms "a plurality" may be understood to include any integer number greater than or equal to two, i.e., two, three, four, five, etc. The term "connection" may include both an indirect "connection" and a direct "connection."

The terms "about," "substantially," "approximately," and variations thereof are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A computer-implemented method comprising:
predicting, by a first machine learning model, a location of an anatomical structure in an input window comprising one or more images from a video of a surgical procedure, the first machine learning model is trained using surgical training data, wherein the first machine learning model predicts the location of the anatomical structure based on a machine-learning generated prediction of a phase of the surgical procedure being performed in the input window, and phase information of the machine-learning generated prediction is used to refine confidence of anatomical structure prediction of the first machine learning model;
predicting, by a second machine learning model, a location of a surgical instrument in the input window, the second machine learning model is trained using the surgical training data;
generating a visualization of the surgical procedure by displaying a first graphical overlay at the location of the anatomical structure and a second graphical overlay at the location of the surgical instrument in the video of the surgical procedure; and
based on a determination that the location of the surgical instrument is within a predetermined threshold from the location of the anatomical structure, providing a user feedback to indicate a proximity of the surgical instrument and the anatomical structure.

2. The computer-implemented method of claim 1, wherein the first machine learning model is trained to predict the location of the anatomical structure associated with a particular type of the surgical procedure.

3. The computer-implemented method of claim 1, wherein the second machine learning model is trained to predict the location of the surgical instrument associated with a particular type of the surgical procedure.

4. The computer-implemented method of claim 1, wherein the second machine learning model predicts the location of the surgical instrument based on an identification of a phase of the surgical procedure being performed.

5. The computer-implemented method of claim 1, wherein determining the proximity of the surgical instrument and the anatomical structure comprises predicting, by a third machine learning model, a depth map of a field of view of the video.

6. The computer-implemented method of claim 1, wherein the first machine learning model uses weak labels, and the second machine learning model uses weak labels and joint detection and segmentation.

7. The computer-implemented method of claim 1, wherein the user feedback is provided based on the anatomical structure being determined as a critical anatomical structure based on one or more attributes of a patient undergoing the surgical procedure.

8. The computer-implemented method of claim 1, wherein one or more visual attributes of the visualization are configured based on a confidence score that is refined using the machine-learning generated prediction of the phase.

9. A system comprising:
a machine learning training system configured to use a training dataset to train:
a first machine learning model to predict a location of an anatomical structure in images from the training dataset; and
a second machine learning model to predict a location of a surgical instrument in the images from the training dataset;
a data collection system configured to capture a video of a surgical procedure;
a model execution system configured to execute the first machine learning model and the second machine learning model to detect the location of the anatomical structure and the location of the surgical instrument in an input window of the video, wherein the first machine earning model predicts the location of the anatomical structure based on a machine-learning generated prediction of a phase of the surgical procedure being performed in the input window, and phase information of the machine-learning generated prediction is used to refine confidence of anatomical structure prediction of the first machine learning model;
an output generator configured to:
based on a determination that the location of the surgical instrument is within a predetermined threshold from the location of the anatomical structure, providing a user feedback by generating a user feedback to indicate a proximity of the surgical instrument and the anatomical structure.

10. The system of claim 9, wherein the first machine learning model is trained to predict the location of the anatomical structure associated with a particular type of the surgical procedure.

11. The system of claim 9, wherein,
the machine learning training system is further configured to train a third machine learning model to predict a depth map of the images from the training dataset;
the model execution system is further configured to execute the third machine learning model to predict the depth map of a field of view of the video; and
the depth map is used to determine that the location of the surgical instrument is within the predetermined threshold from the location of the anatomical structure.

12. The system of claim 9, wherein the output generator is further configured to:
determine a movement vector based on a change in the location of the anatomical structure in the input window of the video;
predict the location of the anatomical structure in a portion of the video that is captured after the input window based on the movement vector; and
displaying the first graphical overlay in a visualization of the video at the predicted location of the anatomical structure.

13. The system of claim 9, wherein the user feedback comprises at least one of a visual, audio, tactile, or haptic feedback.

14. The system of claim 9, wherein one or more visual attributes of a visualization of the output generator are configured based on a confidence score that is refined using the machine-learning generated prediction of the phase, and the confidence score is computed as a distance transform from a central axis of the anatomical structure.

15. A computer program product comprising a memory device having computer executable instructions stored thereon, which when executed by one or more processors cause the one or more processors to perform a method for prediction of features in surgical data using machine learning, the method comprising:
predicting, using an encoder-decoder model, a location of an anatomical structure in an input window comprising one or more images from a video of a surgical procedure, the encoder-decoder model is trained using surgical training data, wherein the encoder-decoder model predicts the location of the anatomical structure based on a prediction of a phase of the surgical procedure being performed;
determining a confidence score of the prediction of the location of the anatomical structure, wherein the prediction of the phase the surgical procedure being performed is used to refine the confidence score of the prediction of the location of the anatomical structure; and
generating a visualization of the surgical procedure by displaying a graphical overlay at the location of the anatomical structure in the video of the surgical procedure, one or more visual attributes of the graphical overlay are configured based on the confidence score.

16. The computer program product of claim 15, wherein the encoder-decoder model is a first encoder-decoder model, and wherein the method further comprises:
predicting, by a second encoder-decoder model, a location of a surgical instrument in the input window, the second encoder-decoder model is trained using the surgical training data; and
based on a determination that the location of the surgical instrument is within a predetermined threshold from the location of the anatomical structure, providing a user feedback in the visualization.

17. The computer program product of claim 16, wherein the user feedback is provided based on the anatomical structure being determined as a critical anatomical structure for the surgical procedure being performed.

18. The computer program product of claim 16, wherein the user feedback is provided by generating, in the visualization of the surgical procedure, a second graphical overlay indicative of a proximity of the surgical instrument and the anatomical structure.

19. The computer program product of claim 18, wherein determining the proximity of the surgical instrument and the anatomical structure comprises, predicting, by a machine learning model, a depth map of a field of view of the video.

20. The computer program product of claim 15, wherein the graphical overlay is displayed in response to the anatomical structure being determined as a critical anatomical structure based for the surgical procedure, and the one or more visual attributes of the graphical overlay comprise color, transparency, shading pattern, text, and outline.

* * * * *